(12) United States Patent
Donnett et al.

(10) Patent No.: US 9,854,985 B2
(45) Date of Patent: Jan. 2, 2018

(54) BRAIN SIGNAL TELEMETRY AND SEIZURE PREDICTION

(75) Inventors: James G. Donnett, St. Albans (GB); Imre Szabo, Pécs (HU); Kalman Mathe, Pecs (HU); Andre Fenton, New York City, NY (US)

(73) Assignee: Bio-Signal Group Corp., Brooklyn, NY (US)

( * ) Notice: Subject to any disclaimer, the term of this patent is extended or adjusted under 35 U.S.C. 154(b) by 2143 days.

(21) Appl. No.: 11/694,816

(22) Filed: Mar. 30, 2007

(65) Prior Publication Data

US 2008/0077039 A1 Mar. 27, 2008

Related U.S. Application Data

(63) Continuation-in-part of application No. 10/425,023, filed on Apr. 28, 2003, now abandoned, which is a continuation-in-part of application No. 10/314,890, filed on Dec. 9, 2002, now abandoned.

(51) Int. Cl.
*A61B 5/04* (2006.01)
*A61B 5/00* (2006.01)
*A61B 5/0478* (2006.01)

(52) U.S. Cl.
CPC ........ *A61B 5/04001* (2013.01); *A61B 5/0006* (2013.01); *A61B 5/0478* (2013.01); *A61B 5/4094* (2013.01); *A61B 5/7232* (2013.01); *A61B 5/7275* (2013.01); *A61B 2560/045* (2013.01)

(58) Field of Classification Search
None
See application file for complete search history.

(56) References Cited

U.S. PATENT DOCUMENTS

| | | | |
|---|---|---|---|
| 3,863,625 | A | 2/1975 | Viglione et al. |
| 4,566,464 | A | 1/1986 | Piccone et al. |
| 5,222,503 | A | 6/1993 | Ives et al. |
| 5,311,876 | A | 5/1994 | Olsen et al. |
| 5,540,235 | A | 7/1996 | Wilson |
| 5,743,860 | A | 4/1998 | Hively et al. |
| 5,791,342 | A | 8/1998 | Woodard |
| 5,857,978 | A | 1/1999 | Hively et al. |
| 5,995,868 | A | 11/1999 | Dorfmeister et al. |
| 6,171,239 | B1 | 1/2001 | Humphrey |
| 6,230,049 | B1 | 5/2001 | Fischell et al. |
| 6,304,775 | B1 | 10/2001 | Iasemidis et al. |
| 6,330,466 | B1 | 12/2001 | Hofmann et al. |
| 6,353,754 | B1 | 3/2002 | Fischell et al. |
| 6,375,614 | B1 | 4/2002 | Braun et al. |
| 6,442,421 | B1 | 8/2002 | Le Van et al. |
| 6,560,486 | B1 | 5/2003 | Osorio et al. |
| 6,658,287 | B1 | 12/2003 | Litt et al. |
| 6,671,555 | B2 * | 12/2003 | Gielen et al. .............. 607/45 |
| 7,346,312 | B2 | 3/2008 | Irazoqui-Pastor et al. |
| 2001/0051819 | A1 | 12/2001 | Fischell et al. |
| 2002/0188217 | A1 | 12/2002 | Farwell |
| 2003/0073917 | A1 | 4/2003 | Echauz et al. |
| 2004/0068199 | A1 | 4/2004 | Echauz et al. |
| 2004/0082875 | A1 | 4/2004 | Donoghue et al. |
| 2004/0138579 | A1 | 7/2004 | Deadwyler et al. |
| 2005/0143589 | A1 | 6/2005 | Donoghue et al. |
| 2006/0111644 | A1 * | 5/2006 | Guttag et al. .............. 600/544 |
| 2006/0206167 | A1 | 9/2006 | Flaherty et al. |
| 2006/0253166 | A1 | 11/2006 | Flaherty et al. |
| 2007/0067003 | A1 | 3/2007 | Sanchez et al. |
| 2008/0243022 | A1 | 10/2008 | Donnett et al. |

FOREIGN PATENT DOCUMENTS

| WO | WO-2005058145 A2 | 6/2005 |
|---|---|---|
| WO | WO-2008/121359 | 10/2008 |
| WO | WO-2008/121361 | 10/2008 |

OTHER PUBLICATIONS

"U.S. Appl. No. 11/694,855, Non Final Office Action dated Feb. 17, 2011", 31 pgs.
"International Application Serial No. PCT/US2008/004126, Preliminary Report on Patentability dated Jul. 3, 2009", 20 pgs.
"International Application Serial No. PCT/US2008/004126, Written Opinion dated Aug. 26, 2008", 10 pgs.
"International Application Serial No. PCT/US2008/004129, International Preliminary Report on Patentability dated Jul. 3, 2009", 21 pgs.
"International Application Serial No. PCT/US2008/004129, International Search Report dated Aug. 26, 2008", 5 pgs.
Bai, Qing , et al., "Single-Unit Neural Recording with Active Microelectrode Arrays", *IEEE Transactions on Biomedical Engineering*, vol. 48, No. 8., (Aug. 2001).
D'Alessandro, M., et al., "Epileptic Seizure Prediction Using hybrid feature selection over multiple intracranial EEG Electrode Contacts: a Report of Four Patients", *IEEE Transactions on Biomedical Engineering,IEEE Service Center* vol. 50,No. 5, (May 1, 2003), 603-615.
Hao, Qu, et al., "A Patient-Specific Alogorithm for the Detection of Seizure Onset in Long-Term EEG Monitoring: Possible Use as a Warning Device", *IEEE Transactions on Biomedical Engineering, IEEE Service Center,*vol. 44, No. 2, (Feb. 1, 1997), 8 pgs.
"U.S. Appl. No. 11/694,855 , Response filed Aug. 15, 2011 to Non Final Office Action dated Feb. 17, 2011", 39 pgs.
"U.S. Appl. No. 11/694,855, Final Office Action dated Sep. 27, 2011", 28 pgs.
"U.S. Appl. No. 11/694,855, Appeal Brief filed Oct. 29, 2012", 38 pgs.
"U.S. Appl. No. 11/694,855, Pre Appeal Brief Request for Review filed Mar. 27, 2012", 5 pgs.

(Continued)

*Primary Examiner* — Russell S Negin
(74) *Attorney, Agent, or Firm* — Schwegman Lundberg & Woessner, P.A.

(57) ABSTRACT

An ambulatory intrinsic brain signal processor circuit is coupled to a plurality of electrodes. The signal processor circuit can include a digital multiplexer circuit coupled to the electrodes to multiplex brain signal data from different electrodes together into a multiplexed data stream. An ambulatory transceiver circuit wirelessly communicates information to and from a remote transceiver. A controller circuit permits a user to control which of the electrodes contribute data, a data resolution, and whether the data includes one or both of neural action or local field potential data. Seizure prediction components and methods are also described.

33 Claims, 14 Drawing Sheets

(56) References Cited

OTHER PUBLICATIONS

"U.S. Appl. No. 11/694,855, Decision on Pre-Appeal Brief dated Apr. 20, 2012", 2 pgs.
"European Application Serial No. 08742375.2, Examination Notification Art. 94(3) dated Jul. 4, 2013", 6 pgs.
"European Application Serial No. 08742375.2, Response filed Oct. 31, 2013 to Examination Notification Art. 94(3) dated Jul. 4, 2013", 19 pgs.

\* cited by examiner

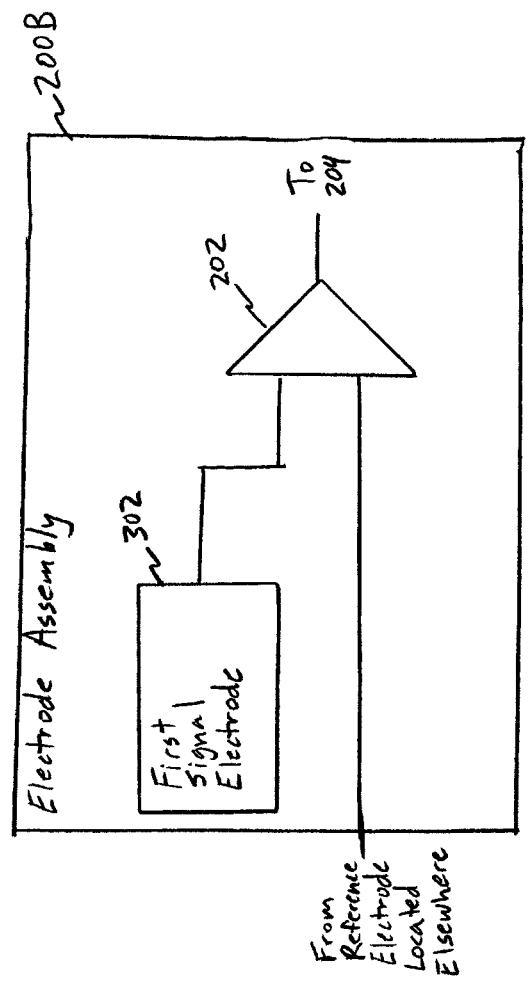

BRAIN SIGNAL TELEMETRY AND SEIZURE PREDICTION

CROSS-REFERENCE TO RELATED PATENT DOCUMENTS

This patent application is a continuation-in-part of U.S. patent application Ser. No. 10/425,023 filed on Apr. 28, 2003 now abandoned, which, in turn, is a continuation-in-part of U.S. patent application Ser. No. 10/314,890, filed Dec. 9, 2002 now abandoned, the specification of each of which is incorporated by reference.

This patent application is related to U.S. patent application Ser. No. 11/694,855, filed on even date herewith, entitled SEIZURE PREDICTION USING BRAIN SIGNAL TELEMETRY, naming James G. Donnett, and André A. Fenton as inventors.

TECHNICAL FIELD

This document pertains generally to brain signal acquisition and telemetry, and more particularly, but not by way of limitation, to systems and methods for acquiring and telemetering one or more brain signals and performing seizure prediction.

BACKGROUND

A very frequent problem in clinical electrophysiology concerns the need to record bioelectric signals, such as the electroencephalogram (EEG), from a subject, and to transmit such signals to a recording device, such as for decoding, analysis, or storage. Using a wired connection between an ambulatory subject and a non-ambulatory recording apparatus is problematic in clinical neurophysiology. A subject undergoing continuous monitoring (for example, for seizure activity) using such a tethered approach would have his or her movement greatly restricted—sometimes for long periods of time. However, a wireless connection will provide limited bandwidth, for example, limited by technological constraints or regulatory allocation of available radio communication frequencies.

OVERVIEW

An ambulatory intrinsic brain signal processor circuit is coupled to a plurality of electrodes. The signal processor circuit can include a digital multiplexer circuit coupled to the electrodes to multiplex brain signal data from different electrodes together into a multiplexed data stream. An ambulatory transceiver circuit wirelessly communicates information to and from a remote transceiver. A controller circuit permits a user to control which of the electrodes contribute data, a data resolution, and whether the data includes one or both of neural action or local field potential data. Seizure prediction components and methods are also described.

Among other things, the present system makes efficient use of limited bandwidth of a wireless communication link between a subject and a remote user interface or other remote monitoring device, such as by:

(i) allowing a user to remotely select a number of channels of brain signal information to be transmitted;

(ii) allowing a user to remotely select a number of bits per channel;

(iii) allowing the user to remotely select a sample rate;

(iv) allowing the user to remotely select a gain of analog-to-digital conversion or pre-process, such as to allow the signal for any channel to be transmitted with a minimal number of bits;

(v) allowing the user to remotely select one of more filtering characteristics, such as according to desired signal type, to permit the dynamic range of the signal to be reduced such that its digitized form can thus be transmitted with fewer bits of resolution; and (vi) allowing the user to store selected data at the subject and only transmit a subset of the data, such as to verify signal integrity.

In Example A1, an apparatus comprises: an ambulatory intrinsic brain signal processor circuit, configured to be coupled to a plurality of electrodes. The signal processor circuit comprises: a digital multiplexer circuit, configured to be coupled to the electrodes, and configured to multiplex brain signal data from different electrodes together into a multiplexed data stream; an ambulatory transceiver circuit, configured to wirelessly communicate information to a remote transceiver, and configured to wirelessly receive user-programming information from the remote transceiver; and a controller circuit, configured to permit a user to control: which of the electrodes contribute data to the multiplexed data stream; a data resolution of the electrodes that contribute data to the multiplexed data stream; and whether data contributed by a particular electrode includes a user-selected one of at least one of: (1) neural action potential data, from which neural field potential data has been reduced or removed; (2) neural field potential data, from which neural action potential data has been reduced or removed; and (3) both neural action potential and neural field potential data.

In Example A2, the apparatus of Example A1, optionally further comprises a plurality of electrode assemblies, each electrode assembly including: at least one electrode, configured to be coupled to a brain of a subject; a brain signal sense amplifier circuit, coupled to the electrode, and configured to sense an intrinsic brain signal and to output a resulting sensed brain signal that is indicative of the intrinsic brain signal; a filter circuit, coupled to the sense amplifier circuit, the filter circuit including a user-programmable frequency filtering characteristic configured to allow a user to select between at least two of: (1) passing neural action potential frequencies; (2) passing neural field potential frequencies; and (3) passing both neural action potential and neural field potential frequencies; and an analog-to-digital converter ("ADC") circuit, coupled to the filter circuit, the ADC configured to digitize brain signal information passed by the filter circuit, the digitizing occurring in close proximity to the electrode.

In Example A3, the apparatus of one or any combination of Examples A1-A2 optionally further includes a sense amplifier circuit that is configured to include: a first input, configured to be coupled to a first signal sensing electrode that is configured for sensing a localized neural action potential signal; a second input, configured to be coupled to a reference signal sensing electrode that is configured for sensing a neural field potential signal; and wherein the amplifier is configured to reduce or remove a common-mode neural field potential signal present between the reference signal sensing electrode and the first signal sensing electrode, and to output a resulting differential signal indicative of a neural action potential.

In Example A4, the apparatus of one or any combination of Examples A1-A3 optionally further includes a sense amplifier circuit that comprises a user-programmable gain.

In Example A5, the apparatus of one or any combination of Examples A1-A4 optionally includes a sense amplifier with a user-programmable gain that includes a neural action potential setting and a neural field potential setting, wherein the neural action potential setting and the neural field potential setting provide different gain values.

In Example A6, the apparatus of one or any combination of Examples A1-A5 optionally include an ADC that comprises a sampling rate and sampling resolution that are both user-programmable.

In Example A7, the apparatus of one or any combination of Examples A1-A6 optionally is configured such that at least one of the sampling rate and the sampling resolution includes a neural action potential setting and a neural field potential setting, wherein the neural action potential setting and the neural field potential setting provide at least one of different sampling rate values and different sampling resolution values.

In Example A8, the apparatus of one or any combination of Examples A1-A7 optionally includes an ambulatory memory device, configured to store brain signal information.

In Example A9, the apparatus of one or any combination of Examples A1-A8 optionally is configured to provide user control over whether a particular electrode's data contribution to the multiplexed data stream is at least one of: provided to the transmitter for communication to remote receiver or provided to the ambulatory memory device for storage.

In Example A10, the apparatus of one or any combination of Examples A1-A9 optionally includes a physiological event detector, communicatively coupled to the controller circuit to trigger at least one of storage or communication of brain signal information in response to detecting a specified physiological event.

In Example A11, the apparatus of one or any combination of Examples A1-A10 optionally is configured to include a physiological event detector that comprises at least one of: (1) a heart rate detector; (2) a neural field potential pattern detector; and (3) a neural action potential pattern detector.

In Example A12, the apparatus of one or any combination of Examples A1-A11 optionally is configured to include a remote user interface comprising: the remote transceiver; a digital demultiplexer circuit, coupled to the remote transceiver; and a user interface controller circuit, coupled to the digital demultiplexer circuit and the remote transceiver, the user interface controller circuit configured to receive a user instruction.

In Example A13, the apparatus of one or any combination of Examples A1-A12 optionally is configured to include a remote user interface that includes at least one of: (1) a digital recorder circuit; and (2) a digital-to-analog converter (DAC) circuit and an analog recorder circuit.

In Example A14, the apparatus of one or any combination of Examples A1-A13 optionally is configured to include a Normal template, providing an indication of correlation of the brain potentials during at least one non-seizure time period of the subject, wherein the non-seizure time period excludes a time period during a seizure, and wherein the non-seizure time period excludes at least a first specified time period preceding the seizure; a Non-Normal template, providing an indication of correlation of the brain potentials during at least one pre-seizure time period or seizure time period of the subject, wherein the pre-seizure time period is less or equal to a second specified time period before the seizure, and wherein the seizure occurs during the seizure time period; a monitoring circuit, configured to form, during a sampling time period, an indication of correlation of the brain potentials using the at least two different locations of a brain of the subject; and an upcoming seizure prediction circuit, configured to predict an upcoming seizure at least in part by comparing the indication of correlation obtained during the sampling time period to each of the Normal and Non-Normal templates.

In Example A15, the apparatus of one or any combination of Examples A1-A14 optionally includes a data integrity circuit, communicatively coupled to receive data contributed by a particular electrode, and configured to determine whether data contributed by a particular electrode includes a valid or useful information about an intrinsic neural signal.

In Example A16, the apparatus of one or any combination of Examples A1-A15 optionally includes a data compression circuit, communicatively coupled to receive data contributed by a particular electrode, and configured to extract parameterized information about a neural event and a corresponding time.

Example A17 includes an apparatus comprising: a plurality of electrode assemblies. Each electrode assembly includes: at least one electrode, configured to be coupled to a brain of a subject; a brain signal sense amplifier circuit, coupled to the electrode, and configured to sense an intrinsic brain signal and to output a resulting sensed brain signal that is indicative of the intrinsic brain signal; a filter circuit, coupled to the sense amplifier circuit, the filter circuit including a user-programmable frequency filtering characteristic configured to allow a user to select between at least two of: (1) passing neural action potential frequencies; (2) passing neural field potential frequencies; and (3) passing both neural action potential and neural field potential frequencies; an analog-to-digital converter ("ADC") circuit, coupled to the filter circuit, the ADC circuit configured to digitize brain signal information passed by the filter circuit, the digitizing occurring in close proximity to the electrode; an ambulatory memory device, configured to store brain signal information; an ambulatory signal processor circuit, coupled to the electrode assemblies. The signal processor circuit includes: a digital multiplexer circuit, coupled to the electrode assemblies, and configured to multiplex data from different electrode assemblies together into a multiplexed data stream; a transceiver circuit, configured to communicate information to a remote transceiver; and a controller circuit. The controller is configured to control the digital multiplexer to permit a user to control: which electrodes contribute data to the multiplexed data stream; a data resolution of each electrode contributing data to the multiplexed data stream; whether a particular electrode's data contribution to the multiplexed data stream is at least one of: provided to the transmitter for communication to the remote receiver or provided to the ambulatory memory device for storage; and whether data contributed by a particular electrode includes a user-selected one of: (1) neural action potential data, from which neural field potential data has been reduced or removed; (2) neural field potential data, from which neural action potential data has been reduced or removed; and (3) both neural action potential and neural field potential data.

Example A18 includes an apparatus comprising: ambulatory means for acquiring brain signals at different locations of a subject's brain; and ambulatory means for receiving information from user input to control: which locations contribute data to a monitored data stream; a data resolution of the locations that contribute data to the monitored data stream; and whether data contributed by a particular location includes a user-selected one of: (1) neural action potential data, from which neural field potential data has been reduced or removed; (2) neural field potential data, from which neural action potential data has been reduced or removed; and (3) both neural action potential and neural field potential data.

Example A19 includes a method that comprises: acquiring brain signals at different locations of an ambulatory subject's brain; receiving, at the ambulatory subject, information from user input to control: which locations contribute data to a monitored data stream; a data resolution of the locations that contribute data to the monitored data stream; and whether data contributed by a particular location includes a user-selected one of: (1) neural action potential data, from which neural field potential data has been reduced or removed; (2) neural field potential data, from which neural action potential data has been reduced or removed; and (3) both neural action potential and neural field potential data.

In Example A20, the method of Example A19 optionally comprises performing, at an assembly carrying an electrode, the acts of sensing an intrinsic brain signal to provide a resulting sensed brain signal that is indicative of the intrinsic brain signal; filtering the sensed brain signal, including configuring a filter characteristic by using user input to select between at least two of: (1) passing neural action potential frequencies; (2) passing neural field potential frequencies; and (3) passing both neural action potential and neural field potential frequencies; and digitizing the filtered sensed brain signal.

In Example A21, the method of one or any combination of Examples A19-A20 optionally includes sensing a first intrinsic brain signal with respect to a reference signal; sensing a second intrinsic brain signal with respect to the reference signal; and combining the first and second intrinsic brain signals into a differential signal indicative of a difference between the first and second intrinsic brain signals and reducing or removing a common mode signal represented by the reference signal.

In Example A22, the method of one or any combination of Examples A19-A21 optionally includes providing, at the subject, a user-programmable gain that includes a neural action potential setting and a neural field potential setting, wherein the neural action potential setting and the neural field potential setting provide different gain values.

In Example A23, the method of one or any combination of Examples A19-A22 optionally includes providing, at the subject, at least one of a user-programmable sampling rate and a user-programmable sampling resolution, wherein at least one of the user-programmable sampling rate and the user-programmable sampling resolution includes a neural action potential setting and a neural field potential setting, wherein the neural action potential setting and the neural field potential setting provide at least one of different sampling rate values and different sampling resolution values.

In Example A24, the method of one or any combination of Examples A19-A23 optionally includes storing, at the subject, brain signal information, including providing user control over whether a particular electrode's data contribution to the monitored data stream is at least one of: provided to the transmitter for communication to the remote receiver or stored at the subject.

In Example A25, the method of one or any combination of Examples A19-A24 optionally includes detecting a physiological event of the subject; and triggering at least one of storage and communication of brain signal information in response to detecting the physiological event.

In Example A26, the method of one or any combination of Examples A19-A25 optionally includes detecting the physiological event comprising at least one of: detecting a heart rate; detecting a specified neural field potential pattern; and detecting a specified neural action potential pattern.

In Example A27, the method of one or any combination of Examples A19-A26 optionally includes: receiving a Normal template providing an indication of correlation of intrinsic brain potentials during at least one non-seizure time period of a subject, wherein the non-seizure time period excludes a seizure time period of a seizure, and wherein the non-seizure time period excludes at least a first specified time period preceding the seizure; receiving a Non-Normal template providing an indication of correlation of the brain potentials during at least one pre-seizure time period or seizure time period of the subject, wherein the pre-seizure time period is less or equal to a second specified time period before the seizure, and wherein the seizure occurs during the seizure time period; monitoring intrinsic brain potentials using at least two different locations of a brain of the subject and forming an indication of correlation of the brain potentials at the at least two different locations during a sampling time period; and predicting an upcoming seizure at least in part by comparing the indication of correlation of the brain potentials obtained during the sampling time period to each of the Normal and Non-Normal templates.

In Example A28, the method of one or any combination of Examples A19-A27 optionally comprises determining whether data contributed by a particular location includes a valid or useful information about an intrinsic neural signal.

In Example A29, the method of one or any combination of Examples A19-A29 optionally comprises extracting, from data contributed by a particular location, parameterized information about a neural event and a corresponding time.

Example B1 includes a method comprising: receiving a Normal template providing an indication of correlation of intrinsic brain potentials during at least one non-seizure time period of a subject, wherein the non-seizure time period excludes a seizure time period of a seizure, and wherein the non-seizure time period excludes at least a first specified time period preceding the seizure; receiving a Non-Normal template providing an indication of correlation of the brain potentials during at least one pre-seizure time period or seizure time period of the subject, wherein the pre-seizure time period is less than or equal to a second specified time period before the seizure, and wherein the seizure occurs during the seizure time period; monitoring intrinsic brain potentials using at least two different locations of a brain of the subject and forming an indication of correlation of the brain potentials at the at least two different locations during a sampling time period; and predicting an upcoming seizure at least in part by comparing the indication of correlation of the brain potentials obtained during the sampling time period to each of the Normal and Non-Normal templates.

In Example B2, the method of Example B1 optionally comprises: receiving a seizure occurrence input to establish a time of at least one known seizure of a subject; monitoring brain potentials using at least two different locations of the brain of the subject; and forming the Normal and Non-Normal templates using information from the monitoring and the time of the at least one known seizure of the subject.

In Example B3, the method of one or any combination of Examples B1-B2 is optionally performed such that the intrinsic brain potentials include local field potentials.

In Example B4, the method of one or any combination of Examples B1-B3 is optionally performed such that the intrinsic brain potentials include intrinsic neuronal action potentials.

In Example B5, the method of one or any combination of Examples B1-B4 is optionally performed such that the monitoring intrinsic brain potentials comprises: acquiring and digitizing neuronal action potential signals at separate locations of different electrodes; communicating information about the digitized action potential signals to an ambulatory transmitter circuit located at the subject; and transmitting information about the digitized action potential signals to at least one of a local or remote user-interface device.

In Example B6, the method of one or any combination of Examples B1-B5 is optionally performed such that the monitoring intrinsic brain potentials comprises monitoring single-unit activity (SUA) of individual neurons.

In Example B7, the method of one or any combination of Examples B1-B6 is optionally performed such that the monitoring intrinsic brain potentials comprises monitoring multi-unit activity (MUA) of a set of nearby individual neurons.

In Example B8, the method of one or any combination of Examples B1-B7 is optionally performed such that the monitoring includes counting a number of neuronal signal energy indications that exceed a specified threshold value.

In Example B9, the method of one or any combination of Examples B1-B8 optionally comprises monitoring that includes integrating a neuronal signal over time.

In Example B10, the method of one or any combination of Examples B1-B9 optionally comprises a first specified time period that is at least one hour.

In Example B11, the method of one or any combination of Examples B1-B10 optionally comprises a second specified time period that is less than or equal to one hour.

In Example B12, the method of one or any combination of Examples B1-B11 optionally comprises at least one of the first and second specified time periods being user-programmable for a particular subject.

In Example B13, the method of one or any combination of Examples B1-B12 optionally comprises at least one of the Normal template, the Non-Normal template, and the forming of the indication of correlation during a sampling time period including measuring a covariance of an brain potential indication using at least two different locations of a brain of the subject.

In Example B14, the method of one or any combination of Examples B1-B13 optionally comprises predicting an upcoming seizure, including: providing a greater likelihood of the upcoming seizure when the indication of correlation obtained during the seizure prediction time becomes less closely matched to the indication of correlation of the Normal template and becomes more closely matched to the indication of correlation of the Non-Normal template; and providing an alert when the likelihood of the upcoming seizure exceeds a specified alert threshold value.

In Example B15, the method of one or any combination of Examples B1-14 optionally comprises receiving a Non-Normal template, comprising receiving a Pre-Seizure template providing an indication of correlation of the brain potentials during at least one pre-seizure time period of the subject, wherein the pre-seizure time period is less or equal to a second specified time period before the seizure.

Example B16 includes an apparatus comprising: means for providing a Normal template providing an indication of correlation of intrinsic brain potentials during at least one non-seizure time period of a subject, wherein the non-seizure time period excludes a seizure time period of a seizure, and wherein the non-seizure time period excludes at least a first specified time period preceding the seizure; means for providing a Non-Normal template providing an indication of correlation of the brain potentials during at least one pre-seizure time period or seizure time period of the subject, wherein the pre-seizure time period is less or equal to a second specified time period before the seizure, and wherein the seizure occurs during the seizure time period; means for monitoring intrinsic brain potentials using at least two different locations of a brain of the subject and forming an indication of correlation of the brain potentials at the at least two different locations during a sampling time period; and means for predicting an upcoming seizure at least in part by comparing the indication of correlation of the brain potentials obtained during the sampling time period to each of the Normal and Non-Normal templates.

In Example B17, the apparatus of Example B16 is optionally configured such that the means for the monitoring brain potentials comprises: separate electrodes, each electrode including an integrated sensing circuit and an integrated digitizing circuit located at that electrode; and an ambulatory transmitter circuit located at the subject, the transmitter circuit communicatively coupled to the electrodes, the transmitter configured for wireless data transmission to a local or remote external receiver.

In Example B18, the apparatus of one or any combination of Examples B16-B17 is optionally configured such that the means for predicting an upcoming seizure using a comparing of the indication of correlation obtained during the sampling time period to each of the Normal and Non-Normal templates comprises: a seizure likelihood indicator that is configured to provide a greater likelihood of the upcoming seizure when the indication of correlation obtained during the seizure prediction time becomes less closely matched to the indication of correlation of the Normal template and more closely matched to the indication of correlation of the Non-Normal template; and an alert comparator circuit, coupled to the seizure likelihood indicator, the alert comparator circuit configured to provide an alert when the likelihood of the upcoming seizure exceeds a specified alert threshold value.

Example B19 includes an apparatus comprising: an intrinsic brain potentials monitor circuit, configured to monitor brain potentials using at least two different locations of a brain of the subject; and a neuronal signal processor circuit, comprising: a Normal template, providing an indication of correlation of the brain potentials during at least one non-seizure time period of the subject, wherein the non-seizure time period excludes a time period during a seizure, and wherein the non-seizure time period excludes at least a first specified time period preceding the seizure; a Non-Normal template, providing an indication of correlation of the brain potentials during at least one pre-seizure time period or seizure time period of the subject, wherein the pre-seizure time period is less or equal to a second specified time period before the seizure, and wherein the seizure occurs during the seizure time period; a monitoring circuit, configured to form, during a sampling time period, an indication of correlation of the brain potentials using the at least two different locations of a brain of the subject; and an upcoming seizure prediction circuit, configured to predict an upcoming seizure at least in part by comparing the indication of correlation obtained during the sampling time period to each of the Normal and Non-Normal templates.

In Example B20, the apparatus of Example B19 optionally comprises a seizure occurrence input, configured to receive information to establish a time of at least one known seizure of a subject for use in forming at least one of the Normal template and the Non-Normal template.

In Example B21, the apparatus of one or any combination of Examples B19-B20 is optionally configured such that the intrinsic brain potentials includes local field potentials.

In Example B22, the apparatus of one or any combination of Examples B19-B21 is optionally configured such that the intrinsic brain potentials include intrinsic neuronal action potentials.

In Example B23, the apparatus of one or any combination of Examples B19-B22 is optionally configured such that the brain potentials monitor circuit comprises: separate electrodes, each electrode including an integrated sensing circuit and an integrated digitizing circuit located at that electrode; and an ambulatory transmitter circuit located at the subject, the transmitter circuit communicatively coupled to the electrodes, the transmitter configured for wireless data transmission to a local or remote external receiver.

In Example B24, the apparatus of one or any combination of Examples B19-B23 is optionally configured such that the brain potentials monitor circuit comprises a multi-unit activity (MUA) monitor circuit configured for monitoring neuronal activity of a set of nearby individual neurons.

In Example B25, the apparatus of one or any combination of Examples B19-B24 optionally comprises a MUA monitor circuit that includes: a signal comparator, configured for determining whether a neuronal signal energy indication exceeds a specified threshold value; and a counter, coupled to the signal comparator, the counter configured to count a number of neuronal signal energy indications that exceed the specified threshold value.

In Example B26, the apparatus of one or any combination of Examples B19-B25 optionally comprises an MUA monitor circuit that comprises a signal integrator configured to integrate a neuronal signal over time.

In Example B27, the apparatus of one or any combination of Examples B19-B26 optionally comprises at least one of the Normal template, the Non-Normal template, and monitoring circuit including a covariance determination circuit configured to measure a covariance of a brain potential indication using at least two different locations of a brain of the subject.

In Example B28, the apparatus of one or any combination of Examples B19-B27 optionally comprises an upcoming seizure prediction circuit that includes: a first comparator circuit, coupled to the Normal template and the monitoring circuit, and configured to compare an indication of correlation obtained during the sampling time period to an indication of correlation associated with the Normal template; a second comparator circuit, coupled to the Non-Normal template and the monitoring correlation circuit, and configured to compare an indication of correlation obtained during the sampling time period to an indication of correlation associated with the Non-Normal template; a seizure likelihood determination circuit, coupled to the first and second comparator circuits, the seizure likelihood determination circuit configured to provide a greater likelihood of the upcoming seizure when the indication of correlation obtained during the seizure prediction becomes less closely matched to the indication of correlation of the Normal template and becomes more closely matched to the indication of correlation of the Non-Normal template; and an alert circuit, configured to provide an alert when the likelihood of the upcoming seizure exceeds a specified alert threshold value.

In Example B29, the apparatus of one or any combination of Examples B19-B28 optionally comprises the Non-Normal template that is a Pre-Seizure template providing an indication of correlation of the brain potentials during at least one pre-seizure time period of the subject, wherein the pre-seizure time period is less or equal to a second specified time period before the seizure.

This overview is intended to provide an overview of the subject matter of the present patent application. It is not intended to provide an exclusive or exhaustive explanation of the invention. The detailed description is included to provide further information about the subject matter of the present patent application.

BRIEF DESCRIPTION OF THE DRAWINGS

In the drawings, which are not necessarily drawn to scale, like numerals may describe substantially similar components in different views. Like numerals having different letter suffixes may represent different instances of substantially similar components. The drawings illustrate generally, by way of example, but not by way of limitation, various embodiments discussed in the present document.

FIG. 3B shows another example of an electrode assembly.

DETAILED DESCRIPTION

The following detailed description includes references to the accompanying drawings, which form a part of the detailed description. The drawings show, by way of illustration, specific embodiments in which the invention may be practiced. These embodiments are also referred to herein as "examples." The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one, independent of any other usages of "at least one" or "one or more." In this document, the term "or" is used to refer to a nonexclusive or, such that "A or B" includes "A but not B," "B but not A," and "A and B," unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Figure 1:
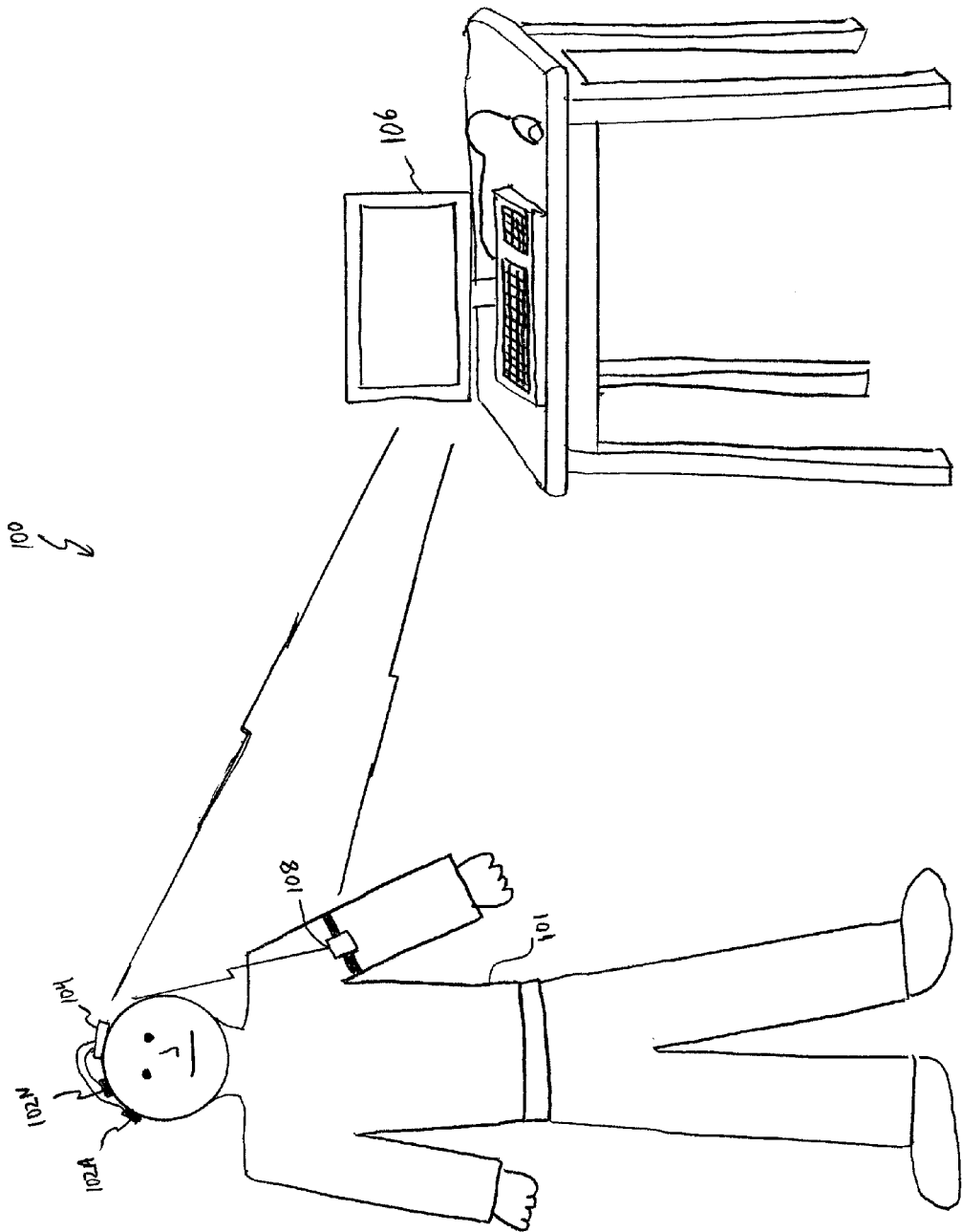
FIG. 1 illustrates generally an example of portions of a brain signal acquisition and processing system, and portions of an environment in which it may be used.

FIG. 1 illustrates generally an example of portions of a brain signal acquisition and processing system 100, and portions of an environment in which it may be used. In this example, the system 100 includes multiple electrodes 102A, ..., 102N at different locations associated with a brain of a subject 101. In various examples, the electrodes 102 can include one or more external skin-patch electrodes or one or more implanted electrodes 102, or any combination of implanted and external electrodes. In the example of FIG. 1, the electrodes 102 are communicatively coupled to an ambulatory brain signal processor circuit 104. In certain examples, this can be accomplished using wires, as shown in FIG. 1. The ambulatory brain signal processor circuit 104 can be adhesively or otherwise attached to the subject's skull, or otherwise attached to the subject 101 or his or her clothing. The ambulatory signal processor circuit 104 includes an ambulatory transceiver that is configured to communicate wirelessly with a remote transceiver of an external remote user interface 106. In certain examples, the wireless communication use radio-frequency (RF) telemetry, such as a BLUETOOTH or other RF link, for example. In certain examples, the wireless communication uses an infrared (IR) or optical wireless link, which can reduce or eliminate the potential for interference with other medical or other equipment, such as patient monitoring equipment that is likely to be present in an intensive care unit or other hospital setting. The remote external user interface 106 is configured to wirelessly receive brain signal information from the ambulatory transceiver of the brain signal processor circuit 104. In the example of FIG. 1, the remote external user interface 106 is also configured to display information to a user and to receive user input from the subject, a caregiver, or another user. The user input can be used, for example, for generating a communication to the ambulatory transceiver of the brain signal processor circuit 104. This can allow the user input to be used for remotely configuring or controlling one or more aspects of brain signal acquisition or signal processing at the subject, such as at one or more of the electrodes 102, or at the brain signal processor circuit 104.

In the example of FIG. 1, the system can also include an ambulatory or other auxiliary sensor, such as auxiliary sensor 108, which is configured to be communicatively coupled to at least one of the brain signal processor circuit 104 or the remote user interface 106. In an ambulatory example of the auxiliary sensor 108, the auxiliary sensor 108 can be communicatively coupled to the brain signal processor circuit 104 by a wired or wireless communication link, or to the remote user interface 106 by a wireless communication link. In a non-ambulatory example of the auxiliary sensor 108, the auxiliary sensor 108 can be communicatively coupled to the remote user interface 106 by a wired or wireless communication link, or to the brain signal processor circuit 104 by a wired communication link. In certain examples, the wireless communication link used by the auxiliary sensor 108 includes a BLUETOOTH or other RF communication link. In certain examples, the auxiliary sensor 108 can be used to provide physiological information about the subject, environmental information, or operational information about the system 100, which can then be used by the system 100 to modify its use. In various examples, the auxiliary sensor includes one or more of: a heart rate detector, an oxygen saturation sensor, a sphygmomanometer or other blood pressure sensor, a body temperature detector, an environmental temperature detector, a weight scale, a patient location detector, a perspiration detector, a posture detector, or any other desired sensor.

Figure 2:
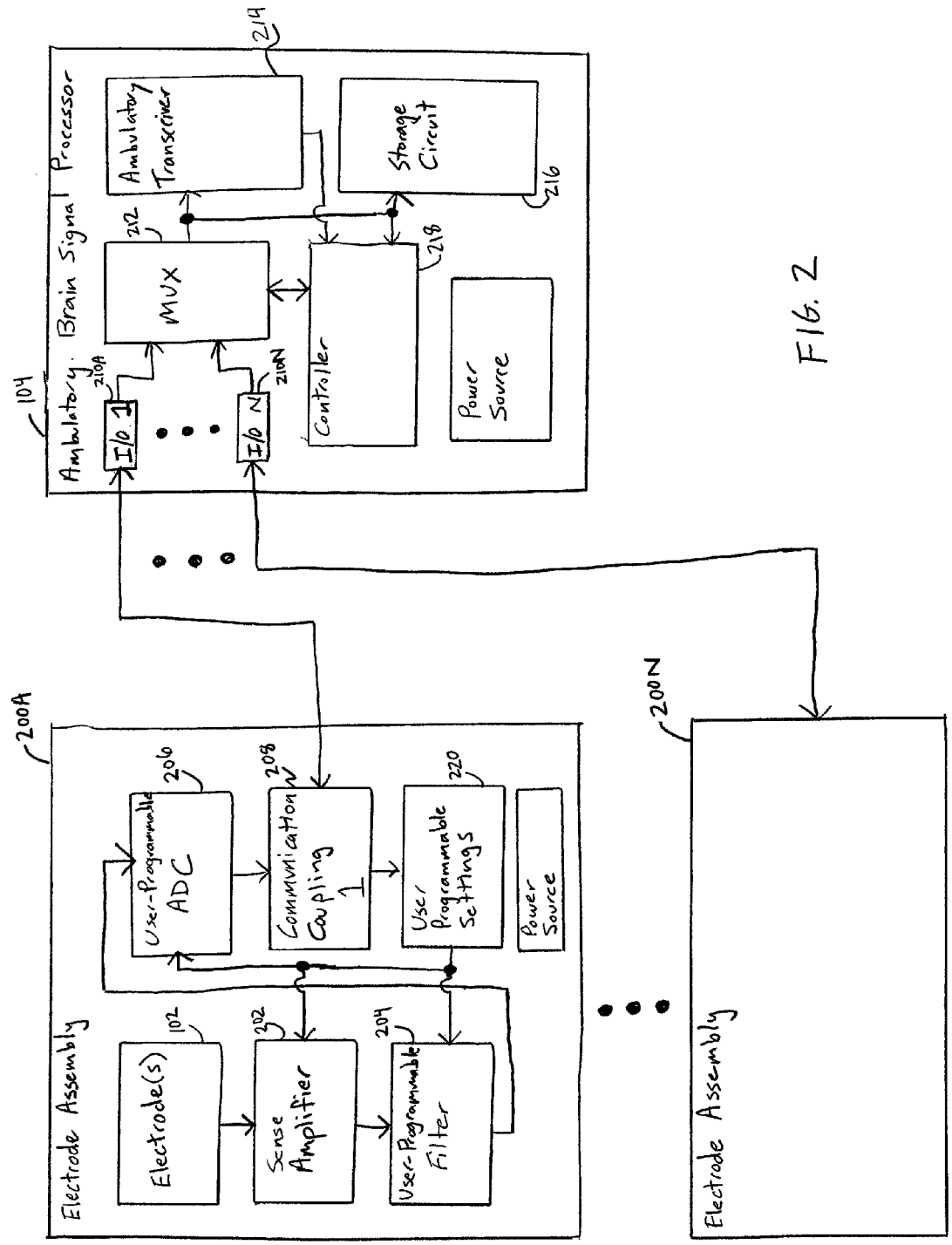
FIG. 2 shows an example of certain ambulatory portions of the system, such as electrode assemblies and an ambulatory brain signal processor.

FIG. 2 shows an example of certain ambulatory portions of the system 100, such as electrode assemblies 200A, ..., 200N and the ambulatory brain signal processor 104. In this example, at least one electrode assembly 200A includes at least one electrode 102, a sense amplifier 202, a user-programmable frequency-selective filter 204, a user-programmable analog-to-digital converter (ADC) circuit 206, and a communication coupling 208. The communication coupling 208 typically includes a connector or the like. This permits bidirectional communication with the ambulatory brain signal processor circuit 104, and can include one or multiple conductors. The electrode assembly 200A provides digitized brain signal information to a corresponding one of input/output communication couplings 210A-N at the ambulatory brain signal processor 104. The digitized brain signal information provided by the electrode assemblies 200 to the input/output couplings 210A-N of the ambulatory brain signal processor 104 is received at a digital signal multiplexer 212. In certain examples, the multiplexer 212 performs time-division multiplexing of this received brain signal information into a multiplexed digital data stream. The multiplexed digital data stream can be provided by the multiplexer 212 to an ambulatory transceiver 214, such as for communicating brain signal information, originally obtained at the multiple electrodes 102, to the user interface 106. In certain examples, the multiplexed digital data stream (or non-multiplexed data from one or more individual electrode assemblies 200) can also be provided to an ambulatory storage circuit 216 for storage. This may be useful, for example, when bandwidth constraints inhibit or preclude communicating the brain signal information to the user interface 106, as well as under other circumstances. Such bandwidth constraints may include, among other things, limited allocation of frequency spectrum (e.g., by a regulatory authority or other entity), sharing of allocated frequency spectrum with other communications devices, a lost or poor quality wireless communications link such as in the presence of interference or if the remote user interface is unavailable or is servicing other subjects. In certain examples, the ambulatory transceiver 214 includes a Quality of Service engine which, in cooperation with a transceiver at the remote user interface 106 attempts to detect and correct any transmission errors, such as by using a checksum or other error detection or correction technique.

User input information can be received at the remote user interface 106. Such user input information can be wirelessly communicated to the ambulatory transceiver 214 of the ambulatory brain signal processor circuit 104. The user information is generally provided to a controller circuit 218. The user information can be used by the controller circuit 218, such as to control operation of the multiplexer 212, for example. The user information can also be routed by the multiplexer circuit 212 to a particular one or more of the electrode assemblies 200. This can provide one or more user programmable settings 220 at a particular electrode assembly 200, which, in turn, can provide user-control over an operational parameter, such as, by way of example, but not by way of limitation: a gain or frequency characteristic of the sense amplifier 202, a gain or frequency characteristic of the filter 204, or a sampling rate or sampling resolution of the ADC circuit 206.

In certain examples, a gain or frequency characteristic of the sense amplifier 202 is user-controllable, at least in part, such as based upon user input information received at a remote user interface 106. In an illustrative example, the user can provide an indication as to whether a particular electrode 102 is to be used to sense neural action potentials, neural field potentials, or both, and that user-provided information is provided to a particular electrode assembly 200 associated with the particular electrode 102 and used to automatically select an appropriate gain or frequency setting of the sense amplifier 202. This can advantageously increase or maximize the dynamic range utilization of the sense amplifier 202 for the particular signal of interest (e.g., neural action potential vs. neural field potential).

For example, neural action potentials typically range in amplitude from between about 50 microvolts to about 500 microvolts, and typically range in frequency from about 300 Hz to about 6 kHz. By contrast, neural field potentials typically range in amplitude from about 500 microvolts to about 5 millivolts, and typically range in frequency from about 0.5 Hz-500 Hz. In certain examples, user input that a particular electrode 102 is to be used to detect neural action potentials can trigger a selectable frequency characteristic of the sense amplifier 202 that helps pass or amplify neural action potential frequencies, helps inhibit or reject neural field potential frequencies, or adjusts the gain of the sense amplifier 202 to help increase or maximize the dynamic range of the sense amplifier 202 as appropriate to neural action potential amplitudes. In certain examples, user input that a particular electrode 102 is to be used to detect neural field potentials can trigger a selectable frequency characteristic of the sense amplifier 202 that helps pass or amplify neural field potential frequencies, helps inhibit or reject neural action potential frequencies, or adjusts the gain of the sense amplifier 202 to help increase or maximize the dynamic range of the sense amplifier 202 as appropriate to neural field potential amplitudes. In certain examples, user input that a particular electrode 102 is to be used to detect both neural field and action potentials can trigger a selectable frequency characteristic of the sense amplifier 202 that helps pass or amplify neural action and field potential frequencies, helps inhibit or reject other frequencies, or adjusts the gain of the sense amplifier 202 to help increase or maximize the dynamic range of the sense amplifier 202 as appropriate to both neural field potential amplitudes and neural action potential amplitudes. In certain examples, the frequency characteristic of the sense amplifier 202, which may in certain examples be implemented as a continuous time circuit, need not be so frequency-selective as to pass neural action potentials while rejecting neural field potentials, but may instead include user-programmability that adjusts the frequency characteristic of the sense amplifier, such as in a manner that is more favorable or less favorable to passing a specified one or both of the neural action potentials or neural field potentials.

In certain examples, the sense amplifier 202 includes an automatic gain control (AGC) circuit to automatically establish a variable gain of the sense amplifier 202. In such an AGC example, the user input as to the particular signal of interest can be used to control or constrain operation of the AGC circuit, such as to control the gain or a frequency characteristic as appropriate for the user-specified signal of interest, e.g., neural action potential, neural field potential, or both neural action potential and neural field potential.

In certain examples, a frequency characteristic of the filter circuit 204 is user controllable, at least in part, such as based upon user input information received at a remote user interface 106. For example, as described above, the user can provide an indication as to whether a particular electrode 102 is to be used to sense neural action potentials, neural field potentials, or both. This information can be used to modify a gain or frequency characteristic of the filter 204, such as to help pass neural action potentials and not neural field potentials, to help pass neural field potentials and not neural action potentials, or to help pass both neural action potentials and neural field potentials. In certain examples, the user information can be used to adjust the value of a resistive, reactive, or other element that contributes to the frequency response of the filter 204. For example, the filter circuit 204 may be a continuous-time circuit or a discrete-time circuit, such as a switched-capacitor circuit. For example, in a switched-capacitor implementation, a programmable capacitor array or clock switching frequency can be used to alter the overall gain or frequency response of the filter 204. In certain examples, the filter circuit 204 includes a highpass filter circuit having a single or multiple pole cutoff frequency at about 300 Hz, such as to pass neural action potential signals, and a lowpass filter circuit having a single or multiple pole cutoff frequency at about 500 Hz, such as to pass neural field potential signals. In certain examples, the filter circuit 204 includes a neural action potential bandpass filter circuit having a single or multiple pole highpass cutoff frequency at around 300 Hz and a single or multiple pole lowpass cutoff frequency at around 6 kHz, such as to pass neural action potential signals, and a neural field potential bandpass filter circuit having a single or multiple pole lowpass cutoff frequency at around 500 Hz and a single or multiple pole highpass cutoff frequency at around 0.5 Hz., such as to pass neural field potentials. In certain examples, the filter circuit 204 further includes a neural action and field potential filter circuit having a single or multiple pole lowpass cutoff frequency at around 6 kHz and a single or multiple pole highpass cutoff frequency at around 0.5 Hz, such as to pass both neural action potentials and neural field potentials. In various examples, the user is able to remotely select which particular filter or filters is applied to processing a brain signal from a particular electrode 102.

In certain examples, a sampling rate or resolution of the ADC circuit 206 is user controllable, at least in part, such as based upon user input information received at a remote user interface 106. For example, as described above, the user can provide an indication as to whether a particular electrode 102 is to be used to sense neural action potentials, neural field potentials, or both. This information can be used to set the sampling rate, for example, to exceed twice the highest frequency of interest to meet the Nyquist criterion and avoid aliasing of the signal of interest, or to obtain a desired degree of oversampling of the user-specified signal of interest. For example, where the user specifies that a particular electrode 102 is to be used to acquire neural action potentials (or both neural action potentials and neural field potentials), a sampling rate of at least 12 kHz may be used. By contrast, if the user specifies that a particular electrode 102 is to be used to acquire neural field potentials and not neural action potentials, a sampling rate of at least 1 kHz may suffice; the lower sampling rate may obtain lower power consumption, and thereby reduce the power demand on an on-board power source included at the particular electrode assembly 200 carrying the particular electrode 102. The user information can additionally or alternatively be used to select a resolution of the digitized signal provided by the ADC circuit 206.

For example, if the user specifies that a particular electrode 120 is to be used to acquire neural action potentials but not neural field potentials, and where the dynamic range of the sense amplifier 202, the filter 204, and the ADC 206 have been automatically set appropriately for acquiring neural action potentials, then 8-bit digitization of the neural action potentials should provide adequate signal resolution and noise margin for the desired neural action potentials. However, if the user specifies that a particular electrode 120 is to be used to acquire both neural action potentials as well as the neural field potentials upon which the neural action potentials are superimposed, and where the dynamic range of the sense amplifier 202, the filter 204, and the ADC 206 are set appropriately for acquiring both neural action potentials and neural field potentials, then 19-24 bit ADC resolution should provide adequate signal resolution and noise margin. In certain examples a 24-bit audio ADC 206 can be used for digitizing a neural signal that includes both neural field potentials and neural action potentials. If the user is able to specify the sampling rate or the data resolution of the ADC, then the user can more effectively use the available bandwidth for communicating between the ambulatory brain signal processor 104 and the remote user interface 106, or the available storage capacity of the storage circuit 216, or the resource utilization of the multiplexer 212 or the ambulatory transceiver 214. This is helpful, particularly as the number of electrodes 102 providing brain signal acquisition increases.

In the example of FIG. 2, the at least one electrode 102 can include multiple electrodes, such as for monopolar or bipolar intrinsic neural signal acquisition, such as of a voltage observed between first and second electrodes. For example, a voltage can be sensed and amplified by a differential amplifier circuit, which typically includes a high input impedance. If the first and second electrodes are located close to each other, the signal acquisition can be conceptualized as bipolar. If the first and second electrodes are not located close to each other, the signal acquisition can be conceptualized as monopolar, as may be the case when multiple individual signal acquisition electrodes at different locations are used with a common reference electrode that serves as a more global reference for the individual signal acquisition electrodes. In another illustrative example, at least one smaller electrode surface area signal acquisition electrode can be used in conjunction with a larger area reference electrode that serves as a more global reference for the at least one smaller electrode surface area signal acquisition electrode. The voltage detected at the larger area reference electrode will be influenced by local intrinsic neural field potentials from a larger region than the region influencing the smaller surface area signal acquisition electrode, which can be sensitive to even more localized neural action potentials.

Figure 3A:
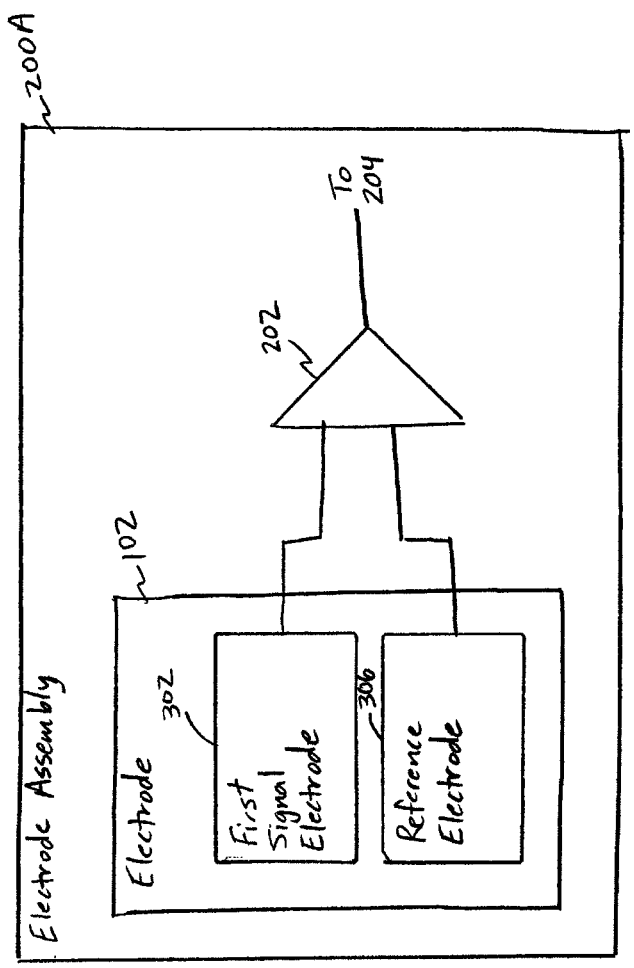
FIG. 3A shows an example of an electrode assembly.

FIG. 3A illustrates generally an example of an electrode assembly 200A that includes electrodes 102, such as a first signal electrode 302 and a reference electrode 306, each of which is fed to an input of a differential amplifier that is included in the sense amplifier 202. An output of the sense amplifier 202 is provided to the filter 204 or other subsequent signal processing circuitry. This example can provide bipolar intrinsic neural signal acquisition or, for example, if the reference electrode 306 is large enough such that it senses a more global reference signal, this example can provide monopolar intrinsic signal acquisition, if desired. Because intrinsic neural action potentials are relatively localized, and intrinsic neural field potentials are relatively more global in nature, using a larger reference electrode 306 with one or more smaller signal sensing electrodes 302 allows acquiring action potentials while attenuating or eliminating the effect of intrinsic neural field potentials. If both intrinsic neural action potentials and intrinsic neural field potentials are desired, this can be obtained using two smaller signal sensing electrodes 302, which will provide a superposition of these two types of signals. The filter 204 can then be user-programmed to selectably pass neural action potentials, neural field potentials, or both neural action potentials and neural field potentials.

FIG. 3B illustrates generally an example of an electrode assembly 200B that includes an electrode 102, such as a first signal electrode 302. In this example, a reference signal is received (e.g., at an input of a differential amplifier included in the sense amplifier 202) from a reference electrode that is not a part of the electrode assembly 200B, but is instead located elsewhere. For example, the reference electrode can be located on another one of the electrode assemblies 200, or the reference electrode can be located with the ambulatory brain signal processor 104. If the reference electrode is located on another one of the electrode assemblies 200, information from the reference signal that it provides can be communicated to the particular electrode assembly 200B either directly, or via the ambulatory brain signal processor 104. In the example of FIG. 3B, the sense amplifier 202 receives as inputs signals from the first signal electrode and the reference electrode, and provides a resulting differential output signal to the filter 204 or other subsequent signal processing circuitry. This example can typically be used to provide monopolar intrinsic signal acquisition, if desired.

Figure 3C:
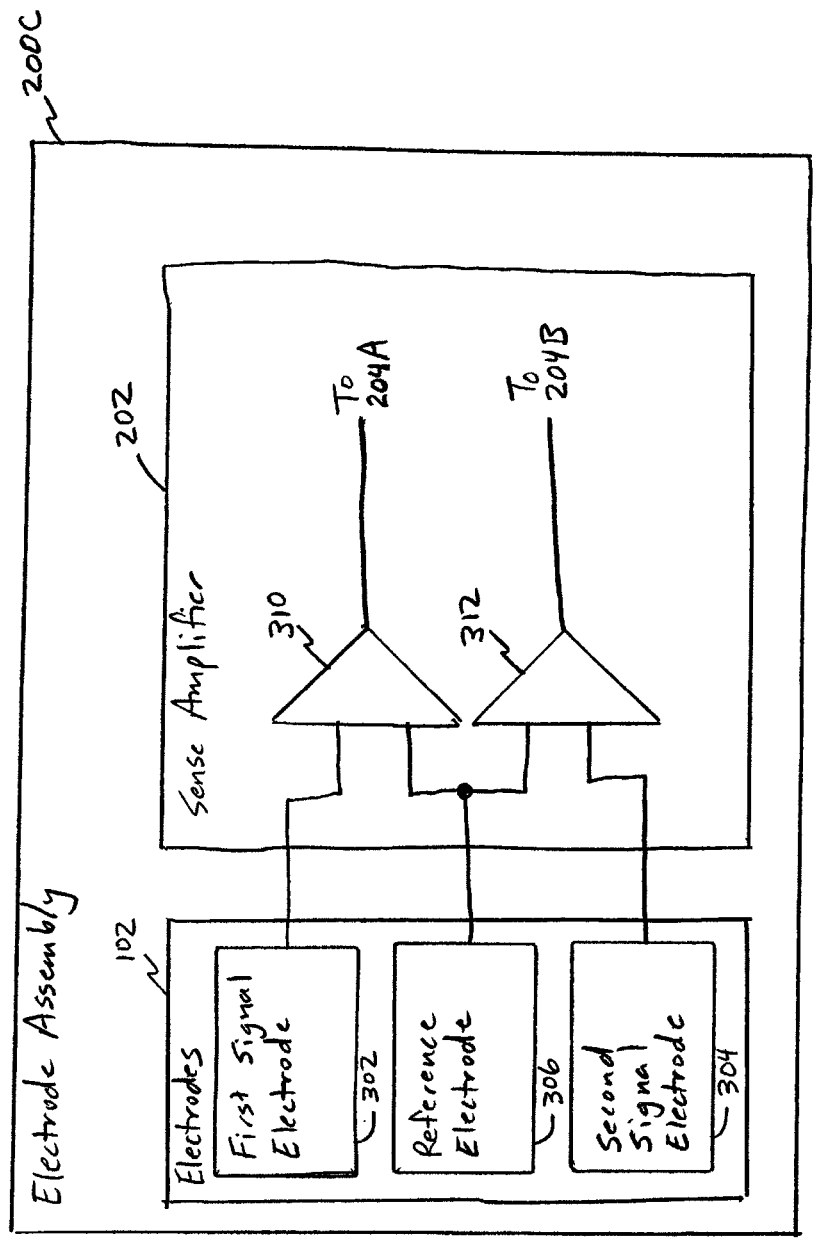
FIG. 3C shows another example of an electrode assembly.

FIG. 3C illustrates generally an example of an electrode assembly 200C that includes electrodes 102, such as a first signal electrode 202, a second signal electrode 204, and a reference electrode 306. The first signal electrode 302 and the reference electrode 306 provide respective signals to a first differential amplifier 310, which is included in the sense amplifier 202, and which provides a resulting differential output signal to the filter 204 or other subsequent signal processing circuitry. The second signal electrode 304 and the reference electrode 306 provide respective signals to a second differential amplifier 312, which is included in the sense amplifier 202, and which provides a separate resulting differential output signal to the filter 204 or other subsequent signal processing circuitry. This example can provide bipolar intrinsic neural signal acquisition or, for example, if the reference electrode 306 is large enough such that it senses a more global reference signal, this example can provide monopolar intrinsic signal acquisition, if desired. Moreover, reference electrode 306 can be omitted and a reference signal can be received from elsewhere, if desired, such as illustrated in FIG. 3B. This would allow multiple reference electrodes 306 to be located in different regions of the brain, such as the hippocampus or various prefrontal cortices. However, having the reference electrode 306 integrated into the same electrode assembly 200C (along with the other electrodes 102 and the sense amplifier 202) advantageously provides better noise immunity.

Figure 3D:
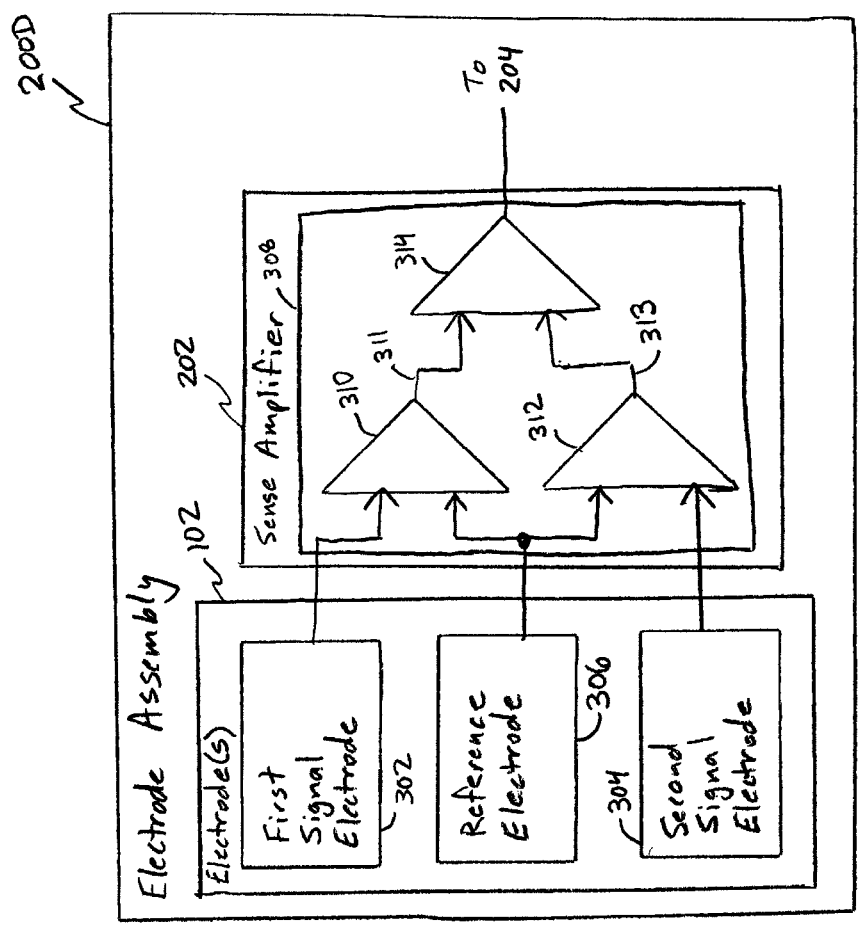
FIG. 3D shows another example of an electrode assembly.

FIG. 3D illustrates generally another example of an electrode assembly 200C in which the at least one electrode 102 includes a first signal electrode 302, a second signal electrode 304, and a reference electrode 306. In this example, the sense amplifier 202 includes an instrumentation amplifier or similar signal acquisition amplifier circuit 308 that performs signal acquisition at least in part by attenuating or rejecting a common-mode signal received at the reference electrode 306, such as for producing at 308 a signal indicative of a difference between the signals observed at the first signal electrode 302 and the second signal electrode 304. For example, the amplifier 308 can include a high input impedance first differential amplifier 310 receiving input signals from the first signal electrode 302 and the reference electrode 306, and producing an output signal at 311 indicative of a difference between these input signals. In this example, the amplifier 308 can include a high input impedance second differential amplifier 312, receiving input signals from the second signal electrode 304 and the reference electrode 306, and producing an output signal at 313 indicative of a difference between these input signals. In this example, a differential amplifier 314 receives the signals at 311 and 313 and outputs at 315 a resulting signal indicative of a difference between the signals observed at the first signal electrode 302 and the second signal electrode 304. Although FIG. 3 illustrates a reference electrode 306 included in the same electrode assembly 200D as a signal electrode, such as the first signal electrode 302 or the second signal electrode 304, in other examples, a signal or reference electrode on a different electrode assembly 200 may be used as a reference electrode, for example, with information about the signal at the reference electrode communicated to a particular electrode assembly 200 from a different electrode assembly 200, such as via the ambulatory signal processor circuit 104. In certain examples, user-information (e.g., provided at the remote user interface 106) is communicated to one or more electrode assemblies 200 to select between bipolar intrinsic neural signal acquisition using first and second electrodes and tripolar intrinsic neural signal acquisition using first and second signal electrodes and a reference signal electrode.

Figure 4:
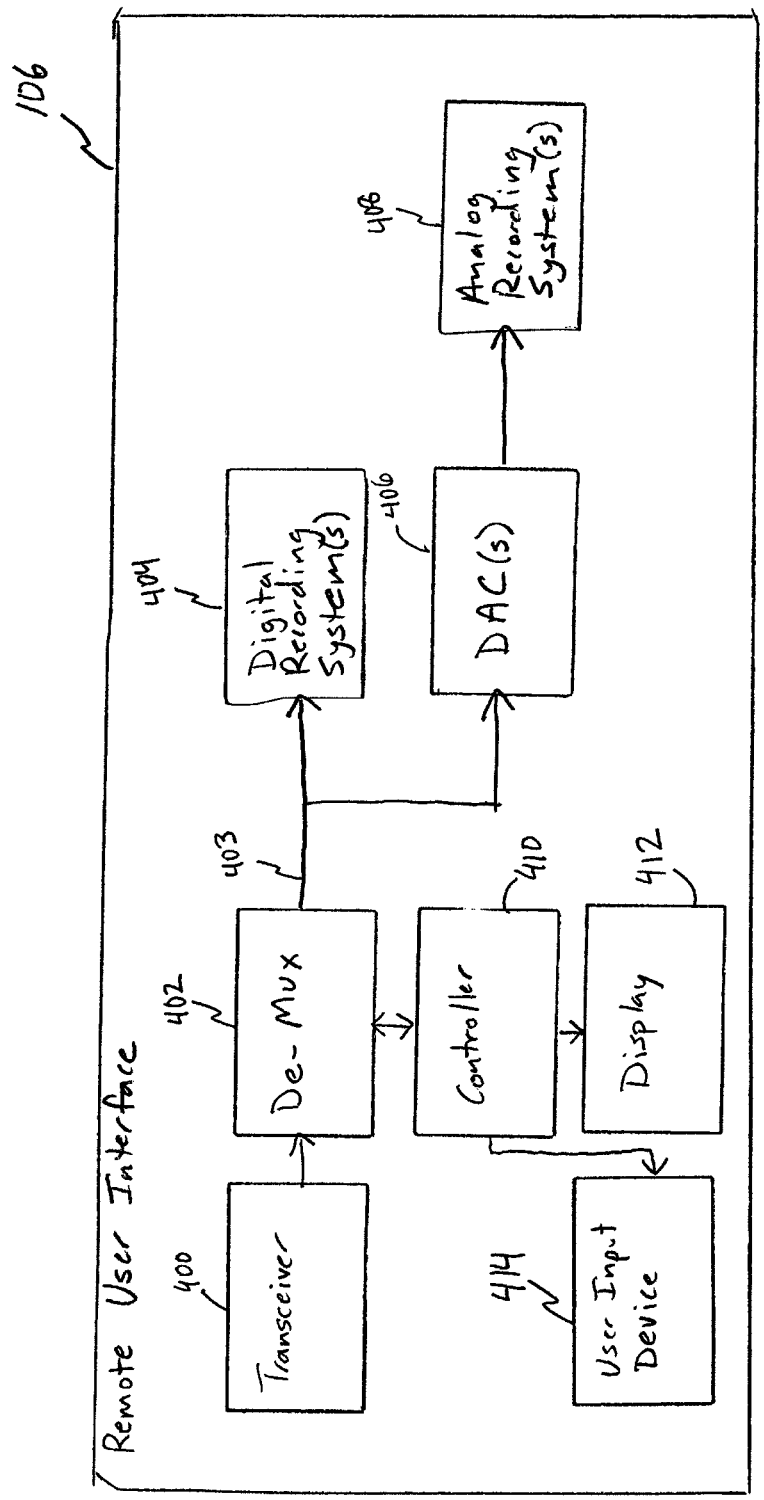
FIG. 4 illustrates an example of portions of a remote user interface.

FIG. 4 illustrates an example of portions of a remote user interface 106. In this example, the remote user interface 106 includes a transceiver 400, configured for wireless communication to the ambulatory transceiver 214, such as for receiving brain signal information or for transmitting user-specified control or configuration parameter information. In certain examples, the transceiver 400 includes a Quality of Service engine, such as to avoid data loss due to radio interference, signal fading, or the like, or to request retransmission of corrupt or missed data. A demultiplexer 402 demultiplexes a time-division multiplexed or other multiplexed data stream received from the ambulatory transceiver 214. The received multiplexed data stream generally represents a user-specified combination of channels, possibly at different resolutions or different sample rates per channel, according to how the multiplexer 212 at the subject 101 was configured, such as by the user. At the remote user interface 106, the demultiplexer 402 splits the received multiplexed data stream, decomposing it into its constituent channels. The resulting demultiplexed parallel data streams at bus 403 are in digital form. These may be sent to a digital recording system 404, such as for storage, display, or analysis. Alternatively, one or more of the signals may be provided to a digital-to-analog converter (DAC) 406 and converted into respective analog signals, such as for being provided to an analog recording system 408, such as for storage, display, or analysis. The remote user interface 106 also generally includes a microprocessor or other controller 410, a display 412, and a user input device 414, such as a computer keyboard, mouse, or the like. This permits the remote user interface to receive user input from the user, such as for configuring operation of the system 100, either at the remote user interface 106, or by providing the information to the ambulatory brain signal processor 104 or to one or more electrode assemblies 200 at the subject 101.

The controller 410 receives control and configuration commands from the user input device 414. In certain examples, it can act on these commands in at least two ways. First, it can control or configure information to the on-subject ambulatory brain signal processor 104 or electrode assemblies 200 via the transceiver 400. Second, it can configure the demultiplexer 402 to match the multiplexing by the multiplexer 212. For example, if the ambulatory brain signal processor 104 is configured to transmit four channels, then the demultiplexer 402 can be similarly programmed to demultiplex the received multiplexed data stream into four channels. The controller 410 can also be used to relay status information sent from the ambulatory brain signal processor 104. In various examples, the controller 410 can be programmed to receive user commands and return status information in any of a variety of ways, including using a Universal Serial Bus (USB), other standard serial port, Ethernet port, parallel port, or the like.

Figure 5:
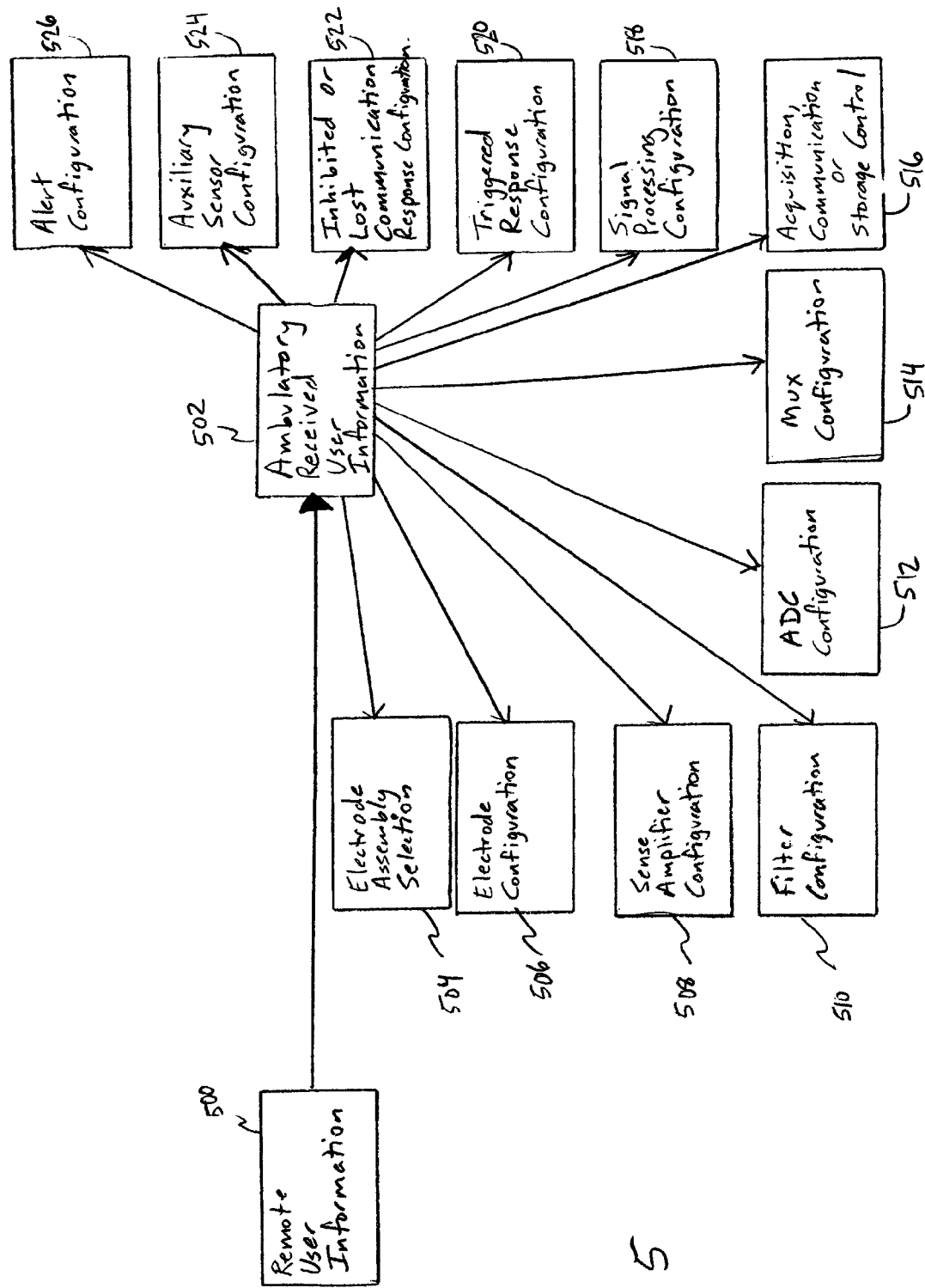
FIG. 5 illustrates certain aspects of user-configurability or system operation.

FIG. 5 illustrates certain aspects of user-configurability or system operation. At 500, user information is received, such as at the remote user interface 106. At 502, the user information is received at the ambulatory subject 101, such as at the ambulatory brain signal processor 104, which, in turn can communicate certain portions of such information to individual electrode assemblies 200, if needed. Receiving user information at the ambulatory subject 101 allows for numerous opportunities to configure the system to better meet the needs of the particular subject 101, rather than merely using default settings available in the absence of such configuration based on such user-provided information.

At 504, the user-provided information can be used for electrode assembly selection, such as to select which particular ones of the electrode assemblies 200 will be used for acquiring respective brain signals; each brain signal that is acquired can be conceptualized as a channel of data. In certain examples, this involves assigning an identifier to each electrode assembly 200 that will be used for acquiring a corresponding brain signal. However, selecting which particular ones of the electrode assemblies 200 will be used for acquiring brain signals need not be a binary decision. For example, this may instead involve an enabling or disabling of intrinsic brain signal acquisition by (or communication from) a particular electrode assembly 200, such as to obtain a desired "duty cycle" with which such intrinsic brain signal information is obtained from a particular electrode assembly 200. For example, it may be desired to obtain intrinsic brain signal information from a specified electrode assembly 200 for 1 minute, followed by an "off" period of 59 minutes, with this repeated every hour. Such a duty cycle can be user-configured, in certain examples. Moreover, in certain examples, such a duty cycle can be user-configured to automatically change upon detecting a particular event or condition. For example, if a condition indicative of a seizure is detected—either at the subject 101 or away from the subject 101, such as at the remote user interface 106—then the user-configuration can be set to automatically select a different signal acquisition duty cycle in response, such as switching over to continuous monitoring, for example.

At 506, the user-provided information can be used for electrode configuration, such as to select which electrode(s) of a particular electrode assembly 200 are used for acquiring intrinsic brain signals, or whether a monopolar, bipolar, tripolar, or other electrode configuration is used for acquiring intrinsic brain signals. For example, if monopolar signals are obtained, they can be later combined at the ambulatory brain signal processor 104 or the remote user interface 106 in any desired combination, such as for signal enhancement or analysis.

At 508, the user-provided information can be used for sense amplifier configuration, such as to select a gain or frequency characteristic of a particular sense amplifier 202 of a particular electrode assembly, such as described above.

At 510, the user-provided information can be used for filter configuration, such as to select a gain or frequency characteristic of a particular filter 204 of a particular electrode assembly 200, such as described above.

At 512, the user-provided information can be used for analog-to-digital conversion configuration, such as to select a sampling rate or a resolution of a particular ADC 206 of a particular electrode assembly 200, such as described above.

At 514, the user-provided information can be used for configuring a multiplexing of brain signal information, such as by configuring the multiplexer 212, such as described above. This can include, for example, deciding which electrode assemblies 200 contribute their acquired brain signal information to a monitored multiplexed signal that is provided as an output from the multiplexer 212, such as described above.

At 516, the user-provided information can be used for configuring or a routing of a particular electrode assembly's brain signal information to the ambulatory transceiver 214, for communication to the remote user interface 106, to the storage circuit 216, for storage, or to the controller 218 for performing further signal processing. The storage circuit 216 generally includes a memory device to locally store at the subject 101 data collected locally at the subject 101, such as for later transmission or uploading to the remote user interface 106. In certain examples, the storage circuit 216 includes a serial memory device such as a Secure Digital card, which can store a multiplexed data stream provided by the multiplexer 212. In other examples, the storage circuit 216 includes a parallel device which can receive and store non-multiplexed data. In certain examples, the multiplexer 212 can be configured to provide either multiplexed or non-multiplexed data to the storage circuit 216. The controller 218 provides one or more control inputs to the storage circuit 216, such as to control starting and stopping of the storage process, or to specify where in the memory the data should be stored or read from. From time to time, the user may remotely provide a command that wirelessly uploads stored information to the remote interface 106. Alternatively, such information can be obtained by removing a memory module from the storage circuit 216 or connecting an conductive cable or optical fiber between the storage circuit 216 and the remote user interface 106. In applications where wireless communication bandwidth is limited, such as where much more intrinsic brain signal data needs to be acquired than can be accommodated by the available wireless communication bandwidth, the data can be stored to the local storage circuit 216, and the wireless communication link to the remote user interface 106 can serve as a monitoring mechanism, allowing the user to step through subsets of data channels while the entire set of channels are being stored at the same time. This would enable the integrity of signals at each electrode to be monitored manually or automatically at the remote user interface unit 106, such as at appropriately selected time intervals. In this way, the loss of recording of sufficiently high quality, such as due to electrode movement or other circumstance, can be detected and used to reconfigure the allocation of resources of the ambulatory brain signal processor 104, such as to exclude one or more signals of poor quality and to use such newly available bandwidth to increase wireless transmission or to reduce power consumption of the ambulatory brain signal processor 104.

At 518, the user-provided information can be used for configuring a signal processing at the subject 101, such as can be performed using the controller 218. In various examples, such signal processing can include physiological event detection, physiological pattern detection or recognition, or other desired signal processing. In certain examples, the controller 218 receives from the multiplexer 212 copies of one or more of its input signals. By performing signal processing on such information, one or more trigger events can be detected.

At 520, the user-provided information can be used for configuring a response that is triggered by a detected physiological or other condition, such as may be detected by the signal processing performed by the controller 218, or as may be detected by signal processing performed remote from the subject 101, such as at the remote user interface 106. This may include mapping a particular response to a specified detected condition. Some illustrative examples of detected conditions include: seizure detected, seizure likelihood detected, wireless communication inhibited, low power detected at the ambulatory brain signal processor 104 or at a particular electrode assembly 200, neural action potential detected at a particular electrode assembly 200, a specified neural signal pattern detected, or the like. Moreover, the auxiliary sensor 108 can also be used to provide the detected condition such as, for example, a specified value or change in value of one or more of heart rate, oxygen saturation, blood pressure, body temperature, environmental temperature, weight, location, perspiration, or any other sensed parameter. Some illustrative examples of detected responses that can be triggered by a specified one or more such conditions include, for example: enabling or disabling wireless communication of brain signal information from at least one specified source; configuring monopolar, bipolar, tripolar, or other brain signal acquisition from at least one specified source; configuring a gain or frequency characteristic of at least one specified sense amplifier 202; configuring a gain or frequency characteristic of at least one specified filter 204; configuring a sampling rate, data resolution, or signal acquisition duty of at least one specified ADC 206, configuring a multiplexing or routing performed by the multiplexer 212; configuring which one or more brain signals are acquired, wirelessly communicated or stored; configuring which signal processing is to be performed in response to a detected condition, or the like.

At 522, the user-provided information can be used for configuring a response to an inhibited or lost wireless communication link, such as between the ambulatory brain signal processor 104 and the remote user interface 106, or between the ambulatory brain signal processor 104 and the auxiliary sensor 108. In certain examples, inhibition or loss of wireless communication between the ambulatory brain signal processor 104 and the remote user interface 106 triggers temporary storage of brain signal information in the storage circuit 216. This may include storage of brain signal waveform information, or may instead include storage of information that is derived from such brain signal waveform information, such as one or more histograms of detected action potentials amplitudes over a specified period of time, which provides a more compact representation of data. In certain examples, the controller 218 is configured to calculate such histograms. In certain examples, actual brain signal waveform information is stored in the storage circuit 216 until an indication of a capacity limitation being reached occurs or is imminent, after which histogram generation by the controller 218 is triggered, and such histogram information is stored in the storage circuit 216. In certain examples, inhibition or loss of wireless communication between the ambulatory brain signal processor 104 and the remote user interface 106 can be configured by the user to disable brain signal acquisition until such wireless communication is re-established. In certain examples, the user can configure the ambulatory brain signal processor circuit 104 to automatically upload data stored in the storage circuit 216 whenever a suitable receiving user interface 106 is found to be within useful communication range.

At 524, the user-provided information can be used for configuring one or more auxiliary sensors 108, such as for use with a particular subject 101, such as to define how the system 100 responds to a physiological or other event detected by that particular auxiliary sensor.

At 526, the user-provided information can be used for configuring an alert to be provided to the subject 101, or to a caregiver (such as via the remote user interface 106). For example, if a seizure is predicted, such as by signal processing performed at the controller 218 or at the remote user interface 106, then an alarm circuit provided at the ambulatory brain signal processor 104 or at an ambulatory auxiliary sensor 108 can be triggered to provide an audible warning to the subject, so that the subject can sit or lie down, insert a mouth protector, or take other protective action. If a seizure is detected, such as by signal processing performed at the controller 218 or at the remote user interface 106, then remote user interface 106 can be used to provide an audible or visual alert to a caregiver monitoring the remote user interface 106, or an emergency service can be called to summon aid for the subject 101. Alerts can also be configured to respond to a non-physiological condition, such as a low-power indication for a power source at the ambulatory brain signal processor or at one of the electrode assemblies 200.

Figure 6:
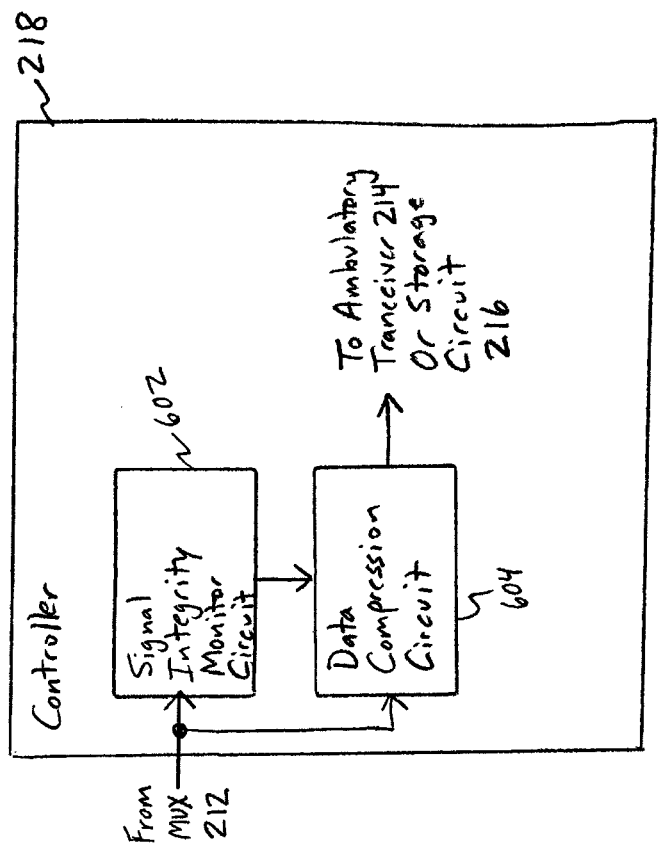
FIG. 6 illustrates generally an example in which the controller of the ambulatory brain signal processor includes at least one of a signal integrity monitor circuit and a data compression circuit.

FIG. 6 illustrates generally an example in which the controller 218 of the ambulatory brain signal processor 104 includes at least one of a signal integrity monitor circuit 602 and a data compression circuit 604. The signal integrity monitor circuit 602 can monitor data being provided by one or more of the electrode assemblies 200, such as to determine whether it is valid or of sufficiently good quality, for example, before it is provided to the ambulatory transceiver 214 or the storage circuit 216. This helps to avoid wasting a limited bandwidth available to the ambulatory transceiver 214 or a limited storage capacity available to the storage circuit 216 by transmitting or storing less than valuable data. The signal integrity monitor circuit 602 can include one or more checks, for example, such as: monitoring a frequency spectrum (e.g., to reject a signal dominated by 50 Hz or 60 Hz power line noise), monitoring an amplitude (e.g., to ensure a minimum signal amplitude or to avoid too large a signal amplitude), monitoring a depolarization or repolarization time potential (e.g., to distinguish between inhibitory and excitatory neural signals), or monitoring a repetition rate of detected events (e.g., a repetition rate of level-detections, peak detections, zero-crossings, or the like). For example, a longer depolarization time period of an intrinsic neural action potential event may represent excitatory neuronal activity, and a shorter depolarization time period of an intrinsic neural action potential events may represent inhibitory neuronal activity. Patterns of correlation between inhibitory and excitatory neurons may be useful information, such as for seizure detection or prediction.

The signal integrity monitor circuit 602 need not be included in the ambulatory brain signal processor 104. Instead, all or a portion of its functionality can be implemented at the remote user interface 106. In such an example, the remote user interface 106 can communicate an instruction back to the ambulatory brain signal processor 104 to cease sending bad or poor data, while occasionally instructing the ambulatory brain signal processor 104 to resume sending data from such source so that it can be determined whether the data continues to be bad or poor, or whether data integrity has been reestablished.

In FIG. 6, a data compression circuit 604 can be provided at the ambulatory brain signal processor 104. For example, intrinsic neural action potential events typically last for between about 0.25 milliseconds and about 2 milliseconds, and can be separated by time period that is on the order of seconds. In certain examples, the data compression circuit 604 can consolidate such sparse information. This can involve extracting information characterizing the 0.25-2 millisecond signal deflection of an intrinsic neural action potential event, and providing a relative or absolute timestamp of its occurrence. In certain examples, the data compression circuit 604 extracts information characterizing the signal deflection of an intrinsic neural action potential event, such as the positive peak amplitude or the negative peak amplitude, or by performing a dimensionality reduction technique such as principal component analysis (PCA) or the like. In certain examples, this permits retaining lower-order principal components that contribute most to the variance or signal deflection of the intrinsic neural action potential event, while disregarding or discarding higher order components. One or more of the retained parameters, along with any timestamp, can then be communicated by the ambulatory transceiver 214 or stored by the storage circuit 216. Other techniques of parameterizing neural action potential events or other events of interest can also be used. By consolidating or compressing the data, available bandwidth or storage capacity can be used more efficiently.

The data compression need not be performed all of the time. In certain examples, the data compression is automatically or manually turned off occasionally, and a non-parameterized or more complete waveform is provided for one or more intrinsic neural action potential events or other events of interest. In certain examples, the user controls whether the data from a particular source is compressed, so that uncompressed data can be reviewed occasionally by the user to ensure its integrity or to diagnose proper or desired system performance.

Seizure Prediction or Detection

The above digital telemetry system examples are suitable for a wide range of applications, such as seizure prediction or detection, examples of which are discussed below, with the understanding that such examples of seizure prediction or detection need not be limited to the particular digital telemetry system examples discussed above.

The brain processes information by the coordinated discharge of action potentials from subsets of neurons, such that individual mental objects like perceptions, ideas and thoughts can be recognized as a pattern of relatively synchronous or coordinated pattern of action potential discharge within a subset of neurons. This can be referred to as "cell assembly." Its consequence is that normal mental operations are characterized by some neurons discharging together, but not at the same time as a different subset of neurons, the discharge of which represents a different mental object. This pattern of neural synchronization and desynchronization characterizes the state of a healthy normally functioning brain.

Epileptic patients have seizures, which are abnormal brain states that are characterized by an unusually high level of neural synchrony within and across brain regions. Therefore, Normal (e.g., non-seizure) and Non-Normal (e.g., seizure or pre-seizure) states of the brain can be distinguished, such as by characterizing the magnitude of neural synchrony within a brain region or across different brain regions.

Based on this reasoning, we describe a way to predict or detect the onset of one or more seizures. In certain examples, the seizure prediction or detection involves monitoring action potential discharge from locations of a brain region that is prone to seizure, such as by using the digital telemetry systems and methods described above, for example. A correlation between action potential discharge in pairs of these locations can be calculated, such as during a sampling time period (e.g., 10 seconds), which can vary from subject to subject. The correlation during the sampling time period can then be compared to a normative or template distribution of this correlation. This comparison can be used to determine the likelihood of a seizure occurring in the near future, such as during a specified prediction time period. In certain examples, the monitored intrinsic action potentials can include monitored single-unit activity (SUA) of individual neurons. In certain examples, the monitored intrinsic action potentials can include monitored multi-unit activity (MUA) of a set of nearby individual neurons. In certain examples, local field potentials are used instead of or in addition to the monitored intrinsic action potentials. The field potentials can generally be conceptualized as representing the effect of intrinsic brain potentials at synapses, rather than the effect of action potentials at the spike initiating zones on cell bodies and along or at axons. This is because the spike initiating zones and axons are not usually very well organized spatially, and the action potentials have positive and negative phases, therefore action potentials from different cells tend to cancel each other out when recorded at a remote site. Synapses, on the other hand, tend to have either a positive or a negative phase. In addition synaptic potential tend to be more well organized in space and time and such that synaptic potentials generally need not cancel each other out.

Figure 7:
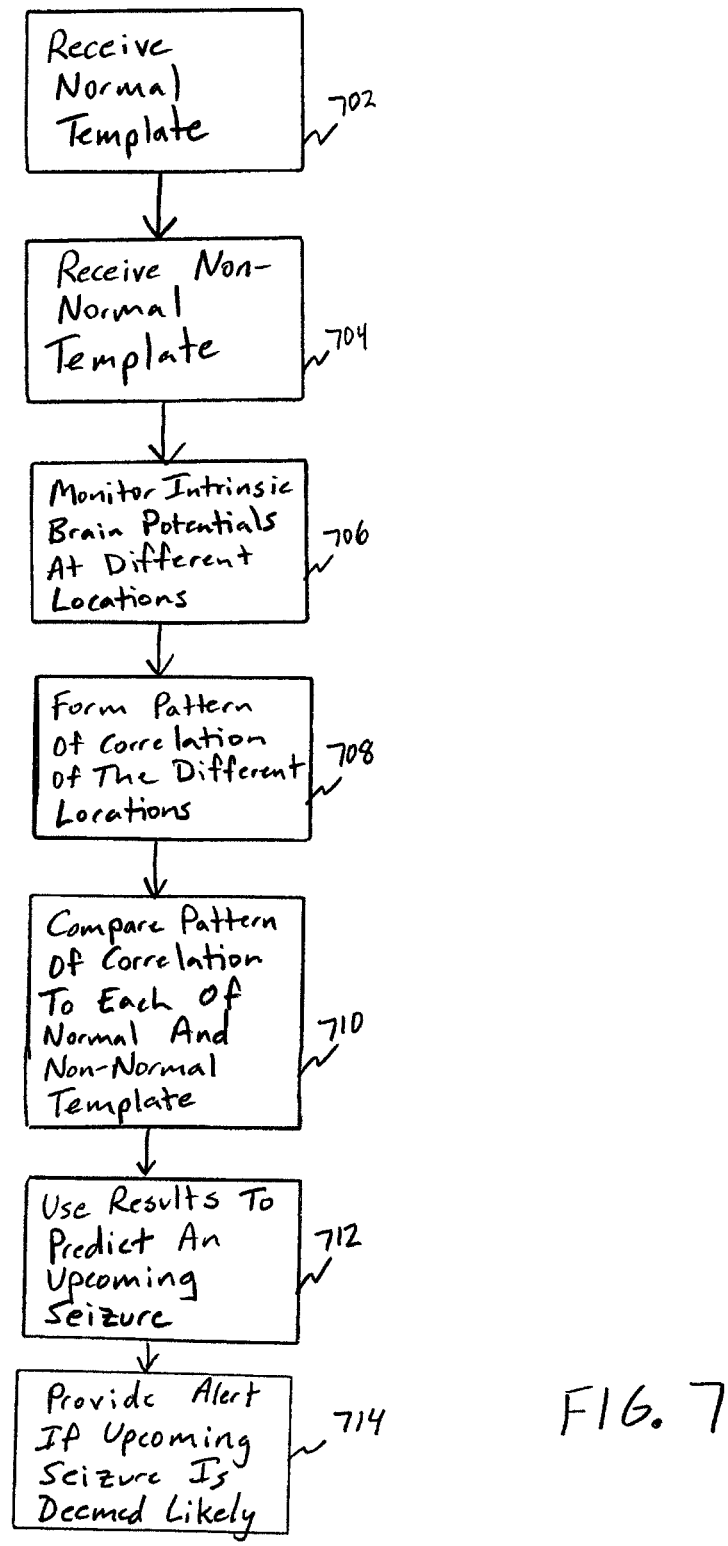
FIG. 7 illustrates generally an example of a seizure prediction technique.

FIG. 7 illustrates generally an example of a seizure prediction technique. At 702, a Normal template is received. The Normal template is indicative of a pattern or other indication of correlation of intrinsic brain potentials during at least one non-seizure time period. The non-seizure time period excludes any time period during which a seizure occurs. The non-seizure time period also typically excludes at least a first specified time period preceding any such known seizure, which will exclude a pre-seizure time period, during which out-of-the-ordinary brain activity may be occurring that could precipitate a seizure. In certain examples, the non-seizure time period excludes a specified at least one hour period preceding any known seizure. In certain examples, this first specified time period is user programmable, such as by using the user interface 106.

The Normal template is typically indicative of a pattern or other indication of correlation of intrinsic brain potentials detected at different locations. In certain examples, the intrinsic brain potentials used to construct the Normal template include intrinsic neuronal action potentials, such as individual intrinsic neuronal action potentials (SUA) detected at different locations or multi-unit activity (MUA) of sets of nearby individual neurons at different locations. In certain examples, the intrinsic brain potentials used to construct the Normal template include intrinsic local field potentials, which typically result from a more global combined effect of many such individual neuronal action potentials or many synaptic potentials. In certain examples, the Normal template includes: (1) a first template pattern or other indication of correlation of intrinsic neuronal action potentials and (2) a second template pattern or other indication of correlation of intrinsic local field potentials.

The pattern or other indication of correlation given by the Normal template can be determined in a number of different ways. In certain examples, it includes determining a covariance between the monitored intrinsic brain signals at the different locations, or determining any indication of how coordinated the intrinsic brain potentials are at the different locations. There are a number of ways that covariance can be computed, such as the Pearson product-moment, for example. The pattern or other indication of correlation can be determined between a pair of locations from which the brain signals are acquired, or between a number N of such locations, which can yield a covariance vector of dimension $N(N-1)/2$, which can form the Normal template.

At 704, a Non-Normal template is received. The Non-Normal template is indicative of a pattern or other indication of correlation of the brain potentials during at least one pre-seizure time period or seizure time period of the subject. For the Non-Normal template, the pre-seizure time period is less than or equal to a second specified time period before a seizure time period during which a seizure occurs. The second specified time period is typically shorter than or equal to the first specified time period, since the first specified time period is used to exclude a pre-seizure time period from the time period used to form the Normal template, and the second specified time period is used to capture a pre-seizure time period in the time period used to form the Non-Normal template. In an illustrative example, a first specified time period of 1 hour before a seizure is excluded from the time period used to form the Normal template, while a second specified time period of 30 minutes before a seizure is included within the time period used to form a Non-Normal template. In certain examples, the Non-Normal template is formed only during a pre-seizure time period, and excludes any seizure time period. In certain examples, the Non-Normal template is formed during a time period that includes both a pre-seizure time period and a seizure time period. In certain examples, the second specified time period is user-programmable, such as by using the user interface 106.

The Non-Normal template is typically indicative of a pattern or other indication of correlation of intrinsic brain potentials detected at different locations. In certain examples, the intrinsic brain potentials used to construct the Non-Normal template include intrinsic neuronal action potentials, such as individual intrinsic neuronal action potentials (SUA) detected at different locations or multi-unit activity (MUA) of sets of nearby individual neurons at different locations. In certain examples, the intrinsic brain potentials used to construct the Non-Normal template include intrinsic local field potentials, which typically result from a more global combined effect of many such individual neuronal action potentials. In certain examples, the Non-Normal template includes: (1) a first template pattern or other indication of correlation of intrinsic neuronal action potentials and (2) a second template pattern or other indication of correlation of intrinsic local field potentials. The pattern or other indication of correlation given by the Non-Normal template can be determined in a manner analogous to that described above for the Normal template.

At 706, intrinsic brain potentials are monitored using at least two different locations of a brain of the subject, such as by using two individual electrode assemblies 200A-B of the system 100, and communicating digitized representations to the ambulatory brain signal processor 104, which, in turn, can relay information to the user interface 106. In certain examples, this involves monitoring intrinsic neuronal action potentials, monitoring intrinsic local field potentials, or both.

At 708, a pattern or other indication of correlation of the different locations being monitored during a sampling time period is determined, such as by using a covariance or the like as described above with respect to the Normal and Non-Normal templates. The covariance vector provides a way to characterize synchrony during a sampling time period at different locations of events of intrinsic brain potentials, such as intrinsic action potentials or intrinsic local field potentials.

At 710, the pattern or other indication of correlation during the sampling time period is compared to each of the Normal and Non-Normal templates to determine its similarity or dissimilarity to each such template. Thus, this comparison can also involve computing a pattern or other indication of correlation to each such template, such as (1) a covariance between the pattern or other indication of correlation obtained during the sampling time period and the pattern or other indication of correlation given by the Normal template, and (2) a covariance between the pattern or other indication of correlation obtained during the sampling time period and the pattern or other indication of correlation given by the Non-Normal template.

At 712, the results of the comparison of 710 are used to predict an upcoming seizure. In certain examples, a decrease of (1), i.e., the covariance between the pattern or other indication of correlation obtained during the sampling time period and the pattern or other indication of correlation given by the Normal template, occurring together with an increase in (2), i.e., the covariance between the pattern or other indication of correlation obtained during the sampling time period and the pattern or other indication of correlation given by the Non-Normal template, is an indication of an increasing likelihood of an upcoming seizure. The decrease in (1) occurring together with the increase in (2) will be more predictive of an upcoming seizure than either a decrease in (1) without a corresponding increase in (2), or an increase in (2) without a corresponding decrease in (1), however, such alternatives can still provide some predictive value for determining whether an upcoming seizure is likely to occur.

At 714, an alert is provided (e.g., to the subject, to a caregiver, to a monitoring service, to emergency medical personnel, or to an automatic drug titration, deep brain stimulation (DBS), or other anti-seizure therapy control module) if an upcoming seizure is deemed likely. In certain examples, an alert of an upcoming seizure is provided when both (1) the covariance between the pattern or other indication of correlation obtained during the sampling time period and the pattern or other indication of correlation given by the Normal template decreases beyond a specified first threshold value, and (2) the covariance between the pattern or other indication of correlation obtained during the sampling time period and the pattern or other indication of correlation given by the Non-Normal template increases beyond a specified second threshold value. This can be done using intrinsic action potentials or using intrinsic local field potentials. This can also be done using both intrinsic action potentials and intrinsic local field potentials, such as by making a separate comparison of each obtained during a sampling time period to respective Normal and Non-Normal templates, each with respective threshold values. Regardless of whether intrinsic action potentials, intrinsic local field potentials, or both are used, the correlations and comparisons can be computed repeatedly, and a trend, a moving average, or the like can be computed, such as to reduce false positive predictions of upcoming seizures.

Figure 8:
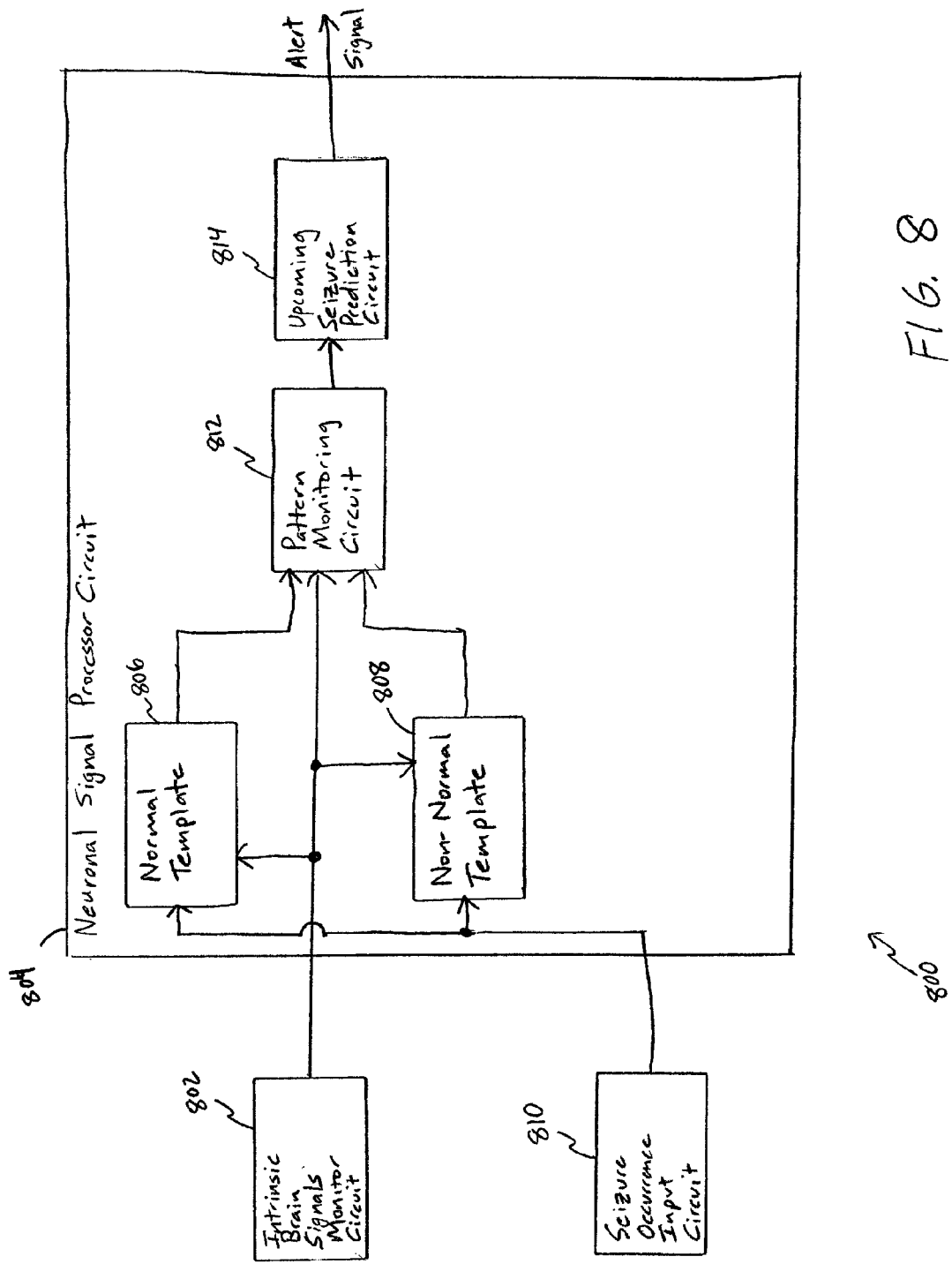
FIG. 8 illustrates generally an example of a system for seizure prediction or detection.

FIG. 8 illustrates generally an example of a system 800 for seizure prediction or detection. In the example of FIG. 8, an intrinsic brain signals monitor circuit 802 is coupled to a neuronal signal processor circuit 804. In certain examples, the intrinsic brain signals monitor circuit 802 can be implemented using the system 100, such as the electrode assemblies 200, the ambulatory brain signal processor 104, and the user interface 106. In certain examples, the neuronal signal processor circuit 804 can be implemented using the controller 218 of the ambulatory brain signal processor 104, using a processor located at the user interface 106, or using a combination of the ambulatory brain signal processor 104 and a processor located at the user interface 106.

In the example of FIG. 8, the neuronal signal processor circuit 804 includes or is coupled to a memory for storing the Normal template 806 and the Non-Normal template 808. In certain examples, a seizure occurrence input circuit 810 is coupled to the neuronal signal processor circuit to provide information about when monitored intrinsic brain signals are indicative of a seizure. In certain examples, the seizure occurrence input circuit is provided by the user interface 106, which a clinician or other user can use to review intrinsic brain signals and classify a time period as representative of a seizure. In an illustrative example, intrinsic brain signals during and for a first specified time period before the seizure time period are excluded when forming the Normal template 806, and intrinsic brain signals occurring during a second specified time period before the seizure time period are included in a Pre-Seizure template, which can be used in forming the Non-Normal template 808, such as described above. In certain examples, brain signals occurring during the seizure time period can be used in forming the Non-Normal template 808.

In the example of FIG. 8, the intrinsic brain signals monitor circuit 802, the Normal template 806, and the Non-Normal template 808 are all coupled to output information to a monitoring circuit 812. The monitoring circuit 812 is configured to compare information about monitored intrinsic brain signals to each of the Normal template 806 and the Non-Normal template 808. Information from the comparison can be provided to an upcoming seizure prediction circuit 814.

As discussed above, in certain examples, if a pattern or other indication of correlation of the monitored intrinsic brain signals becomes less correlated to the Normal template 806 and more correlated to the Non-Normal template 808, then the likelihood of an upcoming seizure increases. In certain examples, the upcoming seizure prediction circuit 814 outputs an alert signal, such as when it determines that the likelihood of an upcoming seizure has increased by a specified amount or beyond a specified threshold value. As discussed above, the alert signal can be used to provide an alert (e.g., to the subject, to a caregiver, to a monitoring service, to emergency medical personnel, or to an automatic drug titration, deep brain stimulation (DBS), or other anti-seizure therapy control module) if an upcoming seizure is deemed likely.

Figure 9:
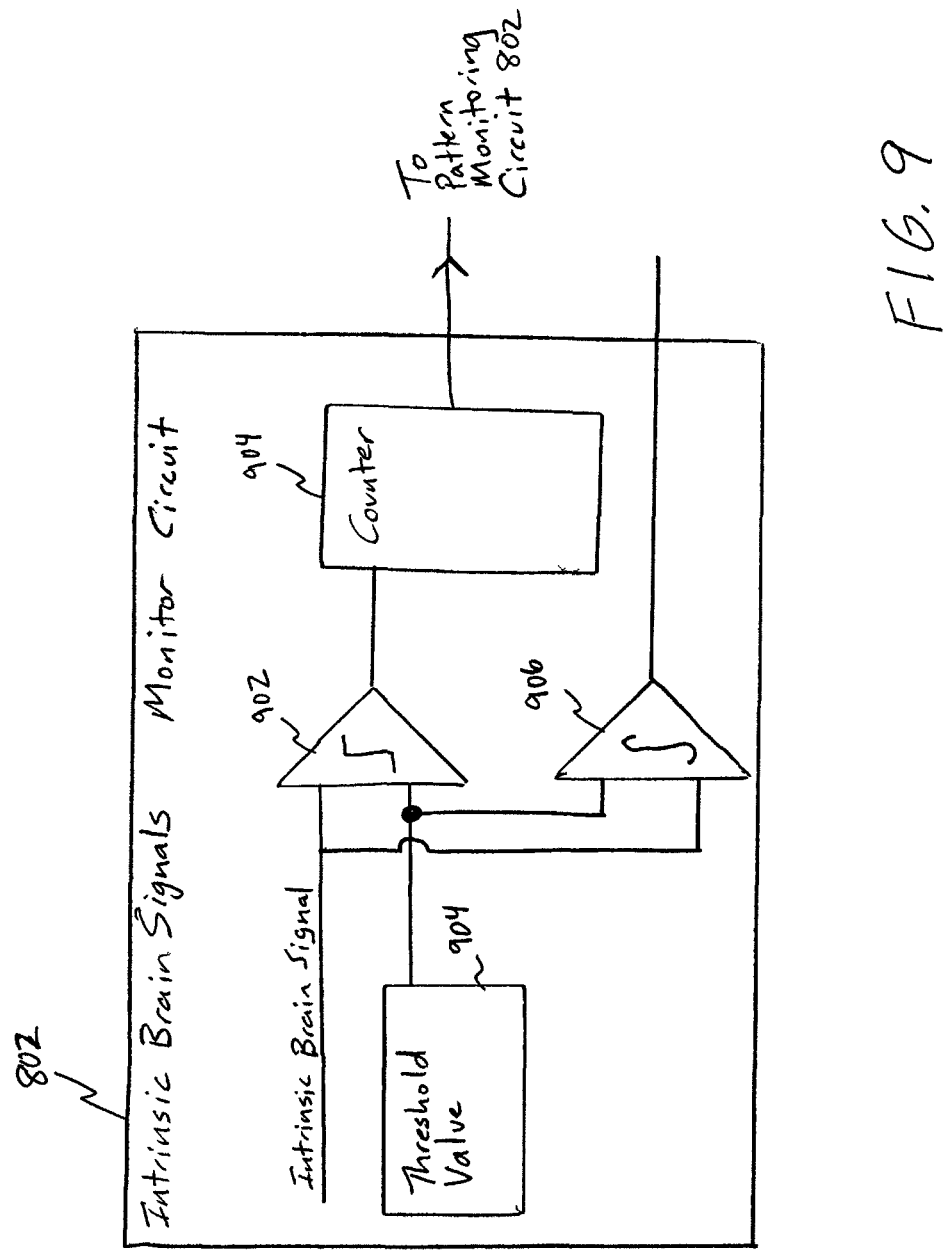
FIG. 9 illustrates generally an example of a portion of the intrinsic brain signals monitor circuit.

FIG. 9 illustrates generally an example of a portion of the intrinsic brain signals monitor circuit 802. In this example, an intrinsic brain signal is received at a comparator circuit 902 for comparison to a threshold value 904. The comparator 902 can be configured to output an indication of an event. As an illustrative example, if the intrinsic brain signal is an intrinsic action potential (e.g., a SUA or MUA), then the comparator 902 can output an indication of an action potential depolarization, which can be provided to a counter 904. The counter 904 can be configured to count action potential depolarizations over a period of time, and can be reset thereafter. The depolarization count can be provided to the monitoring circuit 812, such as for comparison to a depolarization count provided by the Normal template 806 and a depolarization count provided by the Non-Normal template 808. Although FIG. 9 shows a single intrinsic brain signal, comparator 902, and counter 904, this is for illustrative clarity. More typically, multiple intrinsic brain signals (e.g., from different locations) will be monitored, in which case corresponding multiple comparators 902 and counters 904 can be provided, and a correlation between the outputs of such counters 904 can be calculated and provided to the monitoring circuit 812, such as for comparison to the Normal and Non-Normal templates.

In the example of FIG. 9, the intrinsic brain signal can additionally or alternatively be received at an integrator 906. The integrator 906 can be configured to integrate intrinsic brain signal events. As an illustrative example, in which the intrinsic brain signal is a neural action potential, the integrator 906 is configured to also receive as an input the threshold value 904—which can be the same or different from the threshold value used for the comparator 902. In this way, when the neural action potential signal exceeds the threshold value—such as during an intrinsic neural action potential depolarization event—the neural action potential signal is integrated during the depolarization event. Multiple depolarization events over a particular period of time can be similarly integrated, and a resulting output signal provided by the integrator 906. Although FIG. 9 shows a single intrinsic brain signal and integrator 906, this is for illustrative clarity. More typically, multiple intrinsic brain signals (e.g., from different locations) will be monitored, in which case corresponding multiple integrators 906 can be provided, and a correlation between the outputs of such integrators 904 can be calculated and provided to the monitoring circuit 812, such as for comparison to the Normal and Non-Normal templates. Moreover, the integrator(s) 906 can be used in addition to, as an alternative to, or in combination with the comparator(s) 902. For example, if both integrators 906 and comparators 902 are used, separate correlations for the multiple signal acquisition locations can be separately determined for each, and separately compared to respective correlations of the Normal and Non-Normal templates.

Figure 10:
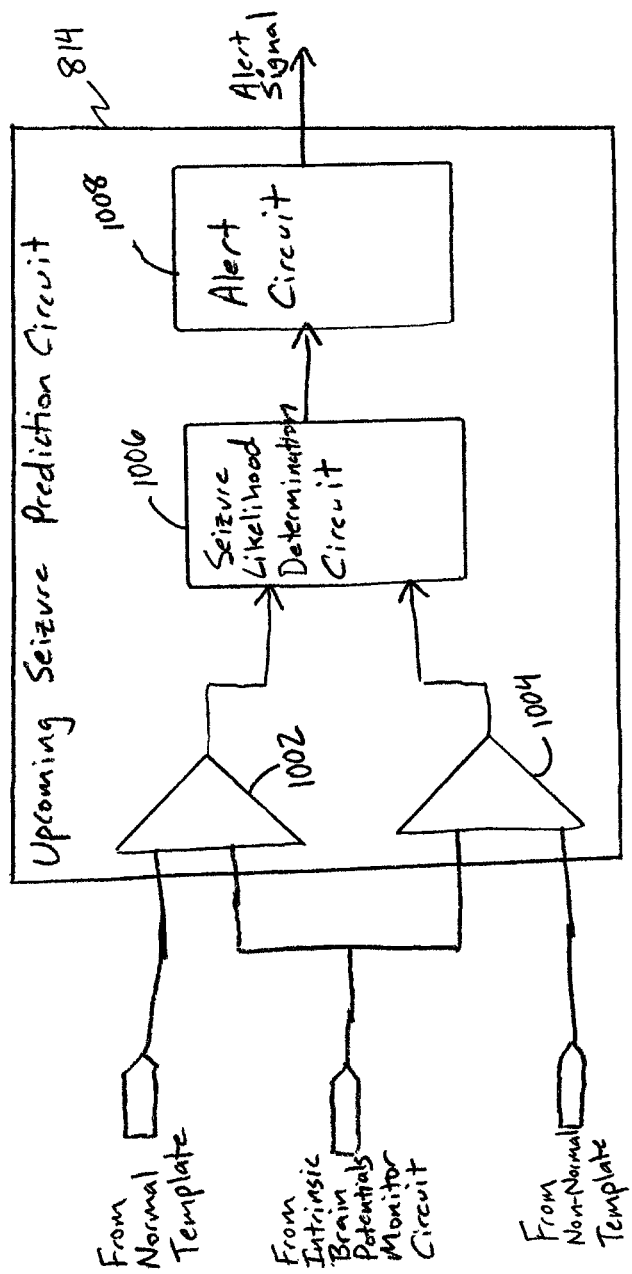
FIG. 10 illustrates generally an example of an upcoming seizure prediction circuit.

FIG. 10 illustrates generally an example of the upcoming seizure prediction circuit 814. In the example of FIG. 10, the upcoming seizure prediction circuit 814 includes a first comparison circuit 1002 and a second comparison circuit 1004, with outputs of each connected to a seizure likelihood determination circuit 1006. The first comparison circuit 1002 receives the pattern or other indication of correlation or other output from the intrinsic brain potentials monitor circuit 802, and compares it to the pattern or other indication of correlation or other information from the Normal template 806. In certain examples, the first comparison circuit 1002 includes a covariance or other correlation circuit that outputs a resulting indication of correlation to the seizure likelihood determination circuit 1006. The second comparison circuit 1004 receives the pattern or other indication of correlation or other output from the intrinsic brain potentials monitor circuit 802, and compares it to the pattern or other indication of correlation or other information from the Non-Normal template 808. In certain examples, the second comparison circuit 1002 includes a covariance or other correlation circuit that outputs a resulting indication of correlation to the seizure likelihood determination circuit 1006.

The seizure likelihood determination circuit 1006 uses information received from the first comparison circuit 1002 and the second comparison circuit 1004 to determine a likelihood of an upcoming seizure. In certain examples, the likelihood of an upcoming seizure is computed as:

$$SL=Ax+By$$

wherein SL is a computed likelihood of an upcoming seizure, x represents an indication of correlation between the Normal template 806 and a pattern or other indication of correlation of intrinsic brain potentials obtained during the sampling time period, y represents an indication of correlation between the Non-Normal template 808 and the pattern or other indication of correlation of intrinsic brain potentials obtained during the sampling time period, and A and B represent positive or negative user-programmable scaling constants.

The alert circuit 1008 uses SL or like information received from the seizure likelihood determination circuit to generate an alert. As an illustrative example, the alert circuit 1008 can include a comparator receiving as inputs SL and a threshold value, and generating an alert when SL exceeds the threshold value. As another illustrative example, the comparator is configured to generate an alert when SL exceeds a baseline value of SL by at least the threshold value. The alert provided by the alert circuit 1008 can be used for various purposes, such as described above.

Figure 11:
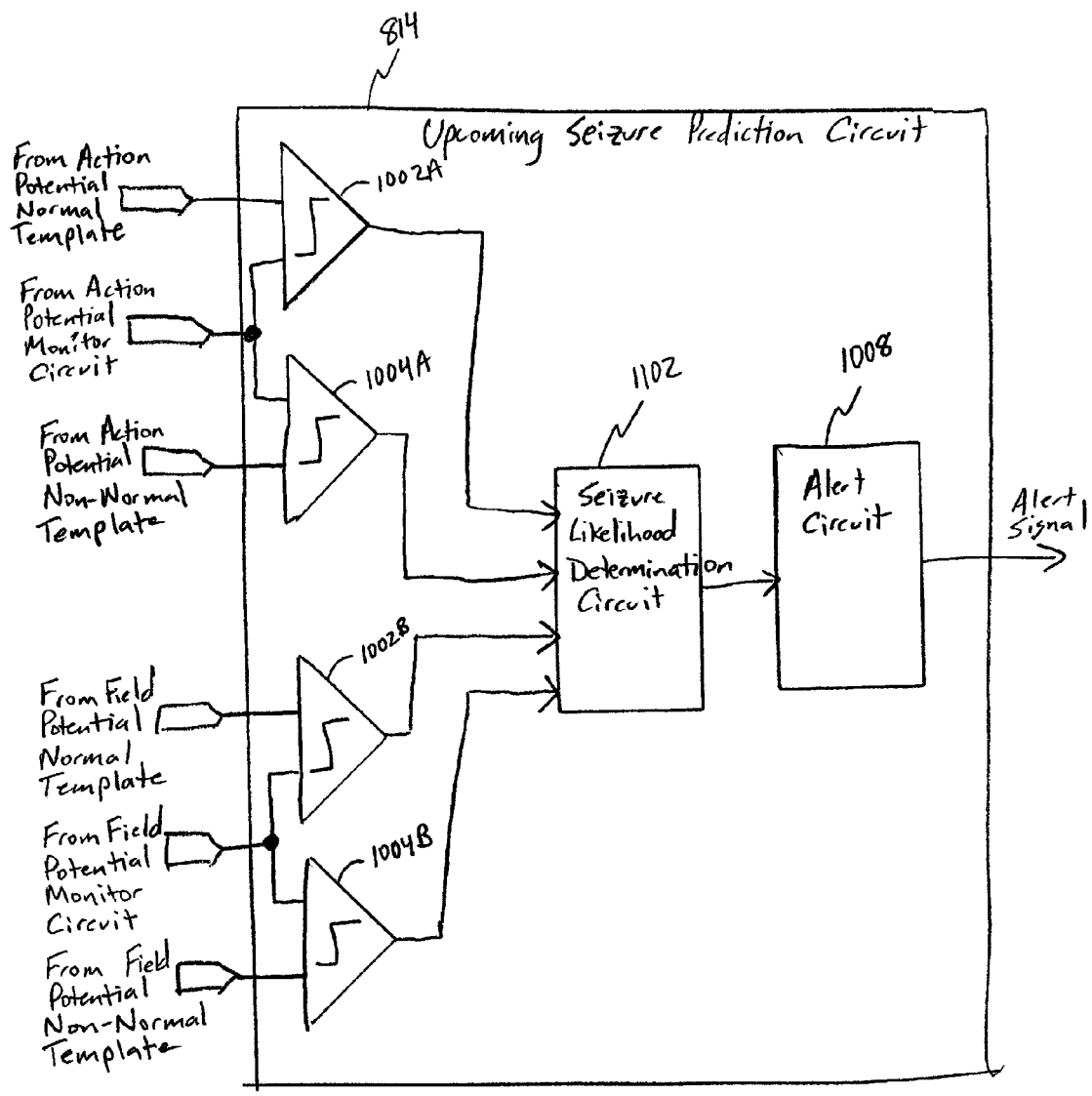
FIG. 11 illustrates generally another example of an upcoming seizure prediction circuit

FIG. 11 illustrates generally another example of the upcoming seizure prediction circuit 814. In this example, the upcoming seizure prediction circuit 814 uses both action potential correlation information and local field potential correlation information. In the example of FIG. 11, comparators 1002A and 1004A can be configured to operate as described with respect to FIG. 10, with a correlation between multiple action potentials being used as the monitored intrinsic brain signals shown in FIG. 10. Comparators 1002B and 1004B are similarly configured, but instead receive a correlation between multiple local field potentials being used as the monitored intrinsic brain signals shown in FIG. 10. In certain examples, the seizure likelihood determination circuit determines a likelihood of an upcoming seizure as:

$$SL=Ax+By+Cz+Dw$$

wherein SL is a computed likelihood of an upcoming seizure, x represents an indication of correlation between an action potential component of the Normal template 806 and a pattern or other indication of correlation of intrinsic action potentials obtained during the sampling time period, y represents an indication of correlation between an action potential component of the Non-Normal template 808 and the pattern or other indication of correlation of intrinsic action potentials obtained during the sampling time period, z represents an indication of correlation between a local field potential component of the Normal template 806 and a pattern or other indication of correlation of intrinsic local field potentials obtained during the sampling time period, w represents an indication of correlation between a local field potential component of the Non-Normal template 808 and the pattern or other indication of correlation of intrinsic local field potentials obtained during the sampling time period, and A, B, C, and D represent user-programmable positive or negative scaling constants. In this example, the alert circuit 1008 of FIG. 11 can be configured to operate in a similar manner to that described with respect to FIG. 10.

The above description is intended to be illustrative, and not restrictive. For example, the above-described embodiments (or one or more aspects thereof) may be used in combination with each other. Other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. §1.72(b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. An apparatus comprising:
   an ambulatory intrinsic brain signal processor circuit, configured to be coupled to a plurality of electrodes, the signal processor circuit comprising:
   a digital multiplexer circuit, configured to be coupled to the electrodes, and configured to multiplex brain signal data from different electrodes together into a multiplexed data stream;
   an ambulatory transceiver circuit, configured to wirelessly communicate information to a remote transceiver, and configured to wirelessly receive user-programming information from the remote transceiver; and
   a controller circuit, configured to:
   select N user-specified electrodes that contribute data to the multiplexed data stream;
   select a data resolution of the electrodes that contribute data to the multiplexed data stream; and
   select, for each particular electrode that contributes data to the multiplexed data stream, one, from between user-selectable choices including all three, of the following settings: (1) neural action potential data, from which neural field potential data has been reduced or removed; (2) neural field potential data, from which neural action potential data has been reduced or removed; and (3) both neural action potential and neural field potential data, and wherein the user-selected one of the three settings is used to automatically select an appropriate gain or frequency setting of a sense amplifier corresponding to the particular electrode; and a Normal template, providing an indication of a set of correlations of brain potentials between all N user-specified electrodes contributing to the multiplexed data stream, during at least one neurologically non-abnormal time period of the subject;
   a Non-Normal template, providing an indication of a set of correlations of the brain potentials between all N user-specified electrodes contributing to the multiplexed data stream, during at least one pre-neurologically-abnormal time period or neurologically abnormal time period of the subject;
   a monitoring circuit, configured to form, during a sampling time period, an indication of a set of correlations of the brain potentials between all N user-specified electrodes contributing to the multiplexed data stream, using the at least two different locations of a brain of the subject; and
   an upcoming neurologically-abnormal-state prediction circuit, configured to predict an upcoming neurologically abnormal state at least in part by comparing the indication of the set of correlations obtained during the sampling time period to each of the Normal and Non-Normal templates.

2. The apparatus of claim 1, further comprising a plurality of electrode assemblies, each electrode assembly including:
   at least one electrode, configured to be coupled to a brain of a subject;
   a brain signal sense amplifier circuit, coupled to the electrode, and configured to sense an intrinsic brain signal and to output a resulting sensed brain signal that is indicative of the intrinsic brain signal;
   a filter circuit, coupled to the sense amplifier circuit, the filter circuit including a user-programmable frequency filtering characteristic configured to allow a user to select one, from between user-selectable choices including all three, of the following settings: (1) passing neural action potential frequencies in a range from about 300 Hz to about 6 kHz; (2) passing neural field potential frequencies in a range from about 0.5 Hz to about 500 Hz; and (3) passing both neural action potential and neural field potential frequencies; and
   an analog-to-digital converter ("ADC") circuit, coupled to the filter circuit, the ADC configured to digitize brain signal information passed by the filter circuit, the digitizing occurring in close proximity to the electrode.

3. The apparatus of claim 2, wherein the sense amplifier circuit is configured to include:
   a first input, configured to be coupled to a first signal sensing electrode that is configured for sensing a localized neural action potential signal;
   a second input, configured to be coupled to a reference signal sensing electrode that is configured for sensing a neural field potential signal; and
   wherein the amplifier is configured to reduce or remove a common-mode neural field potential signal present between the reference signal sensing electrode and the first signal sensing electrode, and to output a resulting differential signal indicative of a neural action potential.

4. The apparatus of claim 2, wherein the sense amplifier circuit comprises a user-programmable gain.

5. The apparatus of claim 4, wherein the user-programmable gain includes a neural action potential setting and a neural field potential setting, wherein the neural action potential setting and the neural field potential setting provide different gain values.

6. The apparatus of claim 2, wherein the ADC comprises a sampling rate and sampling resolution that are both user-programmable for each individual electrode that is specified by the user to contribute to the multiplexed data stream.

7. The apparatus of claim 6, wherein at least one of the sampling rate and the sampling resolution includes a neural action potential setting and a neural field potential setting, wherein the neural action potential setting and the neural field potential setting provide at least one of different sampling rate values and different sampling resolution values.

8. The apparatus of claim 1, further comprising an ambulatory memory device, configured to store brain signal information.

9. The apparatus of claim 8, wherein the controller circuit is configured to provide user control over whether a particular electrode's data contribution to the multiplexed data stream is at least one of: provided to the transmitter for communication to remote receiver or provided to the ambulatory memory device for storage.

10. The apparatus of claim 1, further comprising a physiological event detector, communicatively coupled to the controller circuit to trigger at least one of storage or communication of brain signal information in response to detecting a specified physiological event.

11. The apparatus of claim 10, wherein the physiological event detector comprises at least one of: (1) a heart rate detector; (2) a neural field potential pattern detector; and (3) a neural action potential pattern detector.

12. The apparatus of claim 1, further comprising a remote user interface comprising:
the remote transceiver;
a digital demultiplexer circuit, coupled to the remote transceiver; and
a user interface controller circuit, coupled to the digital demultiplexer circuit and the remote transceiver, the user interface controller circuit configured to receive a user instruction.

13. The apparatus of claim 12, wherein the remote user interface includes at least one of: (1) a digital recorder circuit; and (2) a digital-to-analog converter (DAC) circuit and an analog recorder circuit.

14. The apparatus of claim 1, comprising:
the Normal template providing an indication of a set of correlations of the brain potentials between all N user-specified electrodes contributing to the multiplexed data stream, during at least one non-seizure time period of the subject, wherein the non-seizure time period excludes a time period during a seizure, and wherein the non-seizure time period excludes at least a first specified time period preceding the seizure;
the Non-Normal template providing an indication of a set of correlations of the brain potentials between all N user-specified electrodes contributing to the multiplexed data stream, during at least one pre-seizure time period or seizure time period of the subject, wherein the pre-seizure time period is less or equal to a second specified time period before the seizure, and wherein the seizure occurs during the seizure time period;
the monitoring circuit configured to form, during a sampling time period, an indication of a set of correlations of the brain potentials between all N user-specified electrodes contributing to the multiplexed data stream, using the at least two different locations of a brain of the subject; and
the upcoming neurologically-abnormal-state prediction circuit comprising an upcoming seizure prediction circuit, configured to predict an upcoming seizure at least in part by comparing the indication of the set of correlations obtained during the sampling time period to each of the Normal and Non-Normal templates.

15. The apparatus of claim 1, comprising a data integrity circuit, communicatively coupled to receive data contributed by a particular electrode, and configured to determine whether data contributed by a particular electrode includes a valid or useful information about an intrinsic neural signal.

16. The apparatus of claim 1, comprising a data compression circuit, communicatively coupled to receive data contributed by a particular electrode, and configured to extract parameterized information about a neural event and a corresponding time.

17. The apparatus of claim 1, wherein the upcoming neurologically-abnormal-state prediction circuit is further configured to:
provide an alert to a therapy control module to deliver therapy if an upcoming seizure is predicted.

18. An apparatus comprising:
a plurality of electrode assemblies, each electrode assembly including:
at least one electrode, configured to be coupled to a brain of a subject;
a brain signal sense amplifier circuit, coupled to the electrode, and configured to sense an intrinsic brain signal and to output a resulting sensed brain signal that is indicative of the intrinsic brain signal;
a filter circuit, coupled to the sense amplifier circuit, the filter circuit including a user-programmable frequency filtering characteristic configured to select one, from between user-selectable choices including all three, of the following settings: (1) passing neural action potential frequencies in a range from about 300 Hz to about 6 kHz; (2) passing neural field potential frequencies in a range from about 0.5 Hz to about 500 Hz; and (3) passing both neural action potential and neural field potential frequencies;
an analog-to-digital converter ("ADC") circuit, coupled to the filter circuit, the ADC circuit configured to digitize brain signal information passed by the filter circuit, the digitizing occurring in close proximity to the electrode;
an ambulatory memory device, configured to store brain signal information;
an ambulatory signal processor circuit, coupled to the electrode assemblies, the signal processor circuit including:
a digital multiplexer circuit, coupled to the electrode assemblies, and configured to multiplex data from different electrode assemblies together into a multiplexed data stream;
a transceiver circuit, configured to communicate information to a remote transceiver; and
a controller circuit, configured to control the digital multiplexer to select:
which N user-specified electrodes contribute data to the multiplexed data stream;
a data resolution of each electrode contributing data to the multiplexed data stream;
whether a particular electrode's data contribution to the multiplexed data stream is at least one of: provided to the transmitter for communication to the remote receiver or provided to the ambulatory memory device for storage; and
whether data contributed by a particular electrode includes a user-selected one of user-selectable choices including all three of: (1) neural action potential data, from which neural field potential data has been reduced or removed; (2) neural field potential data, from which neural action potential data has been reduced or removed; and (3) both neural action potential and neural field potential data, wherein the user-selected one of the three choices is used to automatically select an appropriate gain or frequency setting of a sense amplifier corresponding to the particular electrode; and a Normal template, providing an indication of a set of correlations of brain potentials between all N user-specified electrodes contributing to the multiplexed data stream, during at least one neurologically non-abnormal time period of the subject;

a Non-Normal template, providing an indication of a set of correlations of the brain potentials between all N user-specified electrodes contributing to the multiplexed data stream, during at least one pre-neurologically-abnormal time period or neurologically abnormal time period of the subject;

a monitoring circuit, configured to form, during a sampling time period, an indication of a set of correlations of the brain potentials between all N user-specified electrodes contributing to the multiplexed data stream, using the at least two different locations of a brain of the subject; and an upcoming neurologically-abnormal-state prediction circuit, configured to predict an upcoming neurologically abnormal state at least in part by comparing the indication of the set of correlations obtained during the sampling time period to each of the Normal and Non-Normal templates.

19. The apparatus of claim 18, wherein the upcoming neurologically-abnormal-state prediction circuit is further configured to:

provide an alert to a therapy control module to deliver therapy if an upcoming seizure is predicted.

20. An apparatus comprising:

ambulatory means for acquiring brain signals at different locations of a subject's brain; and ambulatory means for receiving information from user input to select: which N user-specified electrodes at the respective different locations contribute data to a monitored data stream; a data resolution of the locations that contribute data to the monitored data stream; and whether data contributed by a particular location includes a user-selected one, from between user-selectable choices including all three of the following: (1) neural action potential data, having frequencies a range from about 300 Hz to about 6 kHz, from which neural field potential data has been reduced or removed; (2) neural field potential data, having frequencies in a range from about 0.5 Hz to about 500 Hz, from which neural action potential data has been reduced or removed; and (3) both neural action potential and neural field potential data, and wherein the user-selected one of the three choices is used to automatically select an appropriate gain or frequency setting of a sense amplifier corresponding to the particular electrode; and a Normal template, providing an indication of a set of correlations of brain potentials between all N user-specified electrodes contributing to the multiplexed data stream, during at least one neurologically non-abnormal time period of the subject;

a Non-Normal template, providing an indication of a set of correlations of the brain potentials between all N user-specified electrodes contributing to the multiplexed data stream, during at least one pre-neurologically-abnormal time period or neurologically abnormal time period of the subject;

a monitoring circuit, configured to form, during a sampling time period, an indication of a set of correlations of the brain potentials between all N user-specified electrodes contributing to the multiplexed data stream, using the at least two different locations of a brain of the subject; and an upcoming neurologically-abnormal-state prediction circuit, configured to predict an upcoming neurologically abnormal state at least in part by comparing the indication of the set of correlations obtained during the sampling time period to each of the Normal and Non-Normal templates.

21. The apparatus of claim 20, wherein the upcoming neurologically-abnormal-state prediction circuit is further configured to:

provide an alert to a therapy control module to deliver therapy if an upcoming seizure is predicted.

22. A method comprising:

acquiring brain signals at different locations of an ambulatory subject's brain;

receiving, at the ambulatory subject, information from user input to control: which N user-selected electrodes at the different locations contribute data to a monitored data stream; a data resolution of the locations that contribute data to the monitored data stream; and whether data contributed by a particular location includes a user-selected one, from between user-selectable choices including all three of: (1) neural action potential data having frequencies in a range from about 300 Hz to about 6 kHz, from which neural field potential data has been reduced or removed; (2) neural field potential data having frequencies in a range from about 0.5 Hz to about 500 Hz, from which neural action potential data has been reduced or removed; and (3) both neural action potential and neural field potential data;

using the user-selected one of the three settings to automatically select an appropriate gain or frequency setting of a sense amplifier corresponding to the particular electrode;

receiving a Normal template providing an indication of a set of correlations between all N user-specified locations that contribute data to the monitored data stream, during at least one neurologically non-abnormal time period of a subject;

receiving a Non-Normal template providing an indication of a set of correlations between all N user-specified locations that contribute data to the monitored data stream, during at least one pre-neurologically-abnormal time period or neurologically abnormal time period of the subject;

monitoring intrinsic brain potentials using at least two different locations of a brain of the subject and forming an indication of a set of correlations of the brain potentials between all N user-specified locations that contribute data to the monitored data stream, including at the at least two different locations during a sampling time period; and predicting an upcoming seizure at least in part by comparing the indication of the set of correlations of the brain potentials obtained during the sampling time period to each of the Normal and Non-Normal templates.

23. The method of claim 22, comprising, at an assembly carrying an electrode:

sensing an intrinsic brain signal to provide a resulting sensed brain signal that is indicative of the intrinsic brain signal;

filtering the sensed brain signal, including configuring a filter characteristic by using user input to select one from user selectable choices including all three of: (1) passing neural action potential frequencies in a range from about 300 Hz to about 6 kHz; (2) passing neural field potential frequencies in a range from about 0.5 Hz to about 500 Hz; and (3) passing both neural action potential and neural field potential frequencies; and digitizing the filtered sensed brain signal.

24. The method of claim 22, comprising:

sensing a first intrinsic brain signal with respect to a reference signal;

sensing a second intrinsic brain signal with respect to the reference signal; and combining the first and second intrinsic brain signals into a differential signal indicative of a difference between the first and second intrinsic brain signals and reducing or removing a common mode signal represented by the reference signal.

25. The method of claim 22, comprising providing, at the subject, a user-programmable gain that includes a neural action potential setting and a neural field potential setting, wherein the neural action potential setting and the neural field potential setting provide different gain values.

26. The method of claim 22, comprising providing, at the subject, at least one of a user-programmable sampling rate and a user-programmable sampling resolution, wherein at least one of the user-programmable sampling rate and the user-programmable sampling resolution includes a neural action potential setting and a neural field potential setting, wherein the neural action potential setting and the neural field potential setting provide at least one of different sampling rate values and different sampling resolution values.

27. The method of claim 22, comprising storing, at the subject, brain signal information, including providing user control over whether a particular electrode's data contribution to the monitored data stream is at least one of: provided to the transmitter for communication to the remote receiver or stored at the subject.

28. The method of claim 22, comprising:

detecting a physiological event of the subject; and triggering at least one of storage and communication of brain signal information in response to detecting the physiological event.

29. The method of claim 28, wherein the detecting the physiological event comprises at least one of: detecting a heart rate; detecting a specified neural field potential pattern; and detecting a specified neural action potential pattern.

30. The method of claim 22, comprising:

receiving the Normal template providing an indication of a set of correlations of brain potentials between all N user-specified locations contributing to the monitored data stream, during at least one non-seizure time period of a subject, wherein the non-seizure time period excludes a seizure time period of a seizure, and wherein the non-seizure time period excludes at least a first specified time period preceding the seizure;

receiving the Non-Normal template providing an indication of the set of correlations of brain potentials between all N user-specified locations contributing to the monitored data stream, during at least one pre-seizure time period or seizure time period of the subject, wherein the pre-seizure time period is less or equal to a second specified time period before the seizure, and wherein the seizure occurs during the seizure time period;

monitoring intrinsic brain potentials using at least two different locations of a brain of the subject and forming an indication of a set of correlations of the brain potentials between all N user-specified locations contributing to the monitored data stream, including at the at least two different locations during a sampling time period; and predicting an upcoming seizure at least in part by comparing the indication of the set of correlations of the brain potentials obtained during the sampling time period to each of the Normal and Non-Normal templates.

31. The method of claim 22, comprising determining whether data contributed by a particular location includes a valid or useful information about an intrinsic neural signal.

32. The method of claim 22, comprising extracting, from data contributed by a particular location, parameterized information about a neural event and a corresponding time.

33. The method of claim 22, comprising:

providing an alert to a therapy control module to deliver therapy if an upcoming seizure is predicted.

* * * * *